(12) United States Patent
Hebrank

(10) Patent No.: US 6,427,844 B2
(45) Date of Patent: *Aug. 6, 2002

(54) METHOD AND APPARATUS FOR SELECTIVELY CLASSIFYING POULTRY EGGS

(75) Inventor: John H. Hebrank, Durham, NC (US)

(73) Assignee: Embrex, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/798,318

(22) Filed: Mar. 2, 2001

Related U.S. Application Data

(63) Continuation of application No. 09/563,218, filed on May 2, 2000, now Pat. No. 6,234,320, which is a continuation-in-part of application No. 09/309,794, filed on May 11, 1999, now abandoned.

(51) Int. Cl.[7] .......................... A01K 43/04; G01N 33/08
(52) U.S. Cl. ....................................... 209/510; 209/511
(58) Field of Search ................................. 209/510, 511

(56) References Cited

U.S. PATENT DOCUMENTS

| | | | | |
|---|---|---|---|---|
| 1,816,483 A | * | 7/1931 | Heaton | |
| 2,175,262 A | * | 10/1939 | Haugh | 88/14.5 |
| 2,520,610 A | * | 8/1950 | Powell | 88/14.5 |
| 2,849,913 A | * | 9/1958 | Bohlman | 88/14.5 |
| 3,060,794 A | * | 10/1962 | Reading | 88/14.8 |
| 3,241,433 A | * | 3/1966 | Niederer, Jr. et al. | 88/14.5 |
| 3,255,660 A | * | 6/1966 | Hirt | 88/14.5 |
| 3,377,989 A | | 4/1968 | Sandhage et al. | 119/1 |
| 3,486,982 A | | 12/1969 | Noren | 195/127 |
| 3,540,824 A | | 11/1970 | Fonda et al. | 356/53 |
| 3,616,262 A | | 10/1971 | Coady et al. | 195/127 |
| 4,040,388 A | | 8/1977 | Miller | 119/1 |
| 4,458,630 A | | 7/1984 | Sharma et al. | 119/1 |
| 4,469,047 A | | 9/1984 | Miller | 119/1 |
| 4,593,646 A | | 6/1986 | Miller et al. | 119/1 |
| 4,671,652 A | | 6/1987 | van Asselt et al. | 356/66 |
| 4,681,063 A | | 7/1987 | Hebrank | 119/1 |
| 4,805,778 A | | 2/1989 | Nambu | 209/3.3 |
| 4,903,635 A | | 2/1990 | Hebrank | 119/1 |
| 4,914,672 A | | 4/1990 | Hebrank | 374/124 |
| 4,955,728 A | | 9/1990 | Hebrank | 374/124 |
| 4,978,225 A | | 12/1990 | Reimer | 356/432 |
| 5,017,003 A | | 5/1991 | Keromnes et al. | 356/53 |
| 5,321,491 A | | 6/1994 | Summers et al. | 356/53 |
| 5,745,228 A | | 4/1998 | Hebrank et al. | 356/53 |
| 5,900,929 A | | 5/1999 | Hebrank et al. | 356/52 |
| 6,234,320 B1 | * | 5/2001 | Hebank | 209/510 |

FOREIGN PATENT DOCUMENTS

GB        969581        9/1964

OTHER PUBLICATIONS

Product Brochure—EPM 650, Automatic Candling and Transfer Machine, INNOVATEC, page Nos. not available, date not available.

Product Brochure—The Invoject® Egg Injection System: Setting the New Worldwide Standard, EMBREX, Inc., page Nos. not available, date not available.

K. Das, et al., Detecting Fertility of Hatching Eggs Using Machine Vision I. Histogram Characterization Method, *American Society of Agricultural Engineers* 35(4) pp 1,335–1,341(1992).

PCT International Search Report dated Aug. 11, 2000 for PCT/US00/12756 (filing date May 10, 2000; priority date May 11, 1999.

* cited by examiner

*Primary Examiner*—Donald P. Walsh
*Assistant Examiner*—Mark J. Beauchaine
(74) *Attorney, Agent, or Firm*—Myers Bigel Sibley & Sajovec

(57) ABSTRACT

An apparatus for classifying a plurality of poultry eggs includes means for detecting the opacities of the eggs, means for detecting the temperatures of the eggs, and means for classifying the eggs using the opacities and the temperatures of the eggs. A method for classifying poultry eggs includes measuring the opacities of the eggs, measuring the temperatures of the eggs, and classifying the eggs as a function of the opacities and the temperatures of the eggs.

20 Claims, 12 Drawing Sheets

METHOD AND APPARATUS FOR SELECTIVELY CLASSIFYING POULTRY EGGS

RELATED APPLICATIONS

This is a continuation application of U.S. Pat. application Ser. No. 09/563,218, filed May 2, 2000 now U.S. Pat. No. 6,234,320, which is a continuation-in-part application of U.S. Pat. application Ser. No. 09/309,794 filed May 11, 1999, now abandoned, the disclosures of which are hereby incorporated herein by reference in their entireties.

FIELD OF THE INVENTION

The present invention concerns methods and apparatus for evaluating and treating poultry eggs, and, in particular, concerns methods and apparatus for non-invasively candling poultry eggs to determine the conditions of the eggs and to handle and treat the eggs in accordance with such determination.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, the contents of the egg can be observed.

In most practices, the purpose of inspecting eggs, particularly "table eggs" for human consumption, is to identify and then segregate those eggs which have a significant quantity of blood present, such eggs themselves sometimes being referred to as "bloods" or "blood eggs." These eggs are less than desirable from a consumer standpoint, making removal of them from any given group of eggs economically desirable.

U.S. Pat. Nos. 4,955,728 and 4,914,672, both to Hebrank, describe a candling apparatus that uses infrared detectors and the infrared radiation emitted from an egg to distinguish live from infertile eggs.

U.S. Pat. No. 4,671,652 to van Asselt et al. describes a candling apparatus in which a plurality of light sources and corresponding light detectors are mounted in an array, and the eggs passed on a flat between the light sources and the light detectors.

In many instances it is desirable to introduce a substance, via in ovo injection, into a living egg prior to hatch. Injections of various substances into avian eggs are employed in the commercial poultry industry to decrease post-hatch mortality rates or increase the growth rates of the hatched bird. Similarly, the injection of virus into live eggs is utilized to propagate virus for use in vaccines. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al., the contents of which are hereby incorporated by reference as if recited in full herein. The selection of both the site and time of injection treatment can also impact the effectiveness of the injected substance, as well as the mortality rate of the injected eggs or treated embryos. See, e.g., U.S. Pat. No. 4,458,630 to Sharma et al., U.S. Pat. No. 4,681,063 to Hebrank, and U.S. Pat. No. 5,158,038 to Sheeks et al. U.S. Patents cited herein are hereby incorporated by reference herein in their entireties.

In ovo injections of substances typically occur by piercing the egg shell to create a hole through the egg shell (e.g., using a punch or drill), extending an injection needle through the hole and into the interior of the egg (and in some cases into the avian embryo contained therein), and injecting the treatment substance through the needle. An example of an injection device designed to inject through the large end of an avian egg is disclosed in U.S. Pat. No. 4,681,063 to Hebrank; this device positions an egg and an injection needle in a fixed relationship to each other, and is designed for the high-speed automated injection of a plurality of eggs. Alternatively, U.S. Pat. No. 4,458,630 to Sharma et al. describes a bottom (small end) injection machine.

In commercial poultry production, only about 50% to 90% of commercial broiler eggs hatch. Eggs that do not hatch include eggs that were not fertilized (which may include rots), as well as fertilized eggs that have died (often classified into early deads, mid-deads, rots, and late deads). Infertile eggs may comprise from about 5% up to about 25% of all eggs set. Due to the number of dead and infertile eggs encountered in commercial poultry production, the increasing use of automated methods for in ovo injection, and the cost of treatment substances, an automated method for identifying, in a plurality of eggs, those eggs that are suitable for injection and selectively injecting only those eggs identified as suitable, is desirable.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-viable. Non-viable eggs are manually removed before the eggs are conveyed to the inoculating station.

SUMMARY OF THE INVENTION

According to embodiments of the present invention, a method for classifying poultry eggs includes providing a plurality of eggs each having a respective physical egg location, measuring the opacities of the eggs, measuring the temperatures of the eggs, and classifying the eggs as a function of the opacities and the temperatures of the eggs. The step of classifying includes identifying clear eggs of the plurality of eggs using the opacities of the eggs, determining a spatial temperature trend among the plurality of eggs using the identification of the clear eggs, and identifying live eggs of the plurality of eggs using the spatial temperature trend.

Preferably, the step of determining a spatial temperature trend includes generating a temperature trend map including a predicted egg temperature for each egg location. The step of identifying the live eggs may include comparing the measured temperatures and the predicted temperatures.

The step of classifying may include correcting the egg temperatures for relative egg locations using the identification of the clear eggs, and identifying live eggs of the plurality of eggs using the corrected egg temperatures. The step of identifying live eggs may include determining a threshold temperature, comparing the corrected egg temperatures to the threshold temperature, and classifying the eggs having a corrected egg temperature greater than the threshold temperature as live.

The method may include identifying upside-down eggs and excluding the temperatures of the upside-down eggs from the temperature trend determination.

According to further embodiments of the present invention, a method for classifying poultry eggs includes measuring the opacities of the eggs, measuring the temperatures of the eggs, and classifying the eggs as a function of the opacities and the temperatures of the eggs. The step of classifying includes identifying clear eggs of the plurality of eggs using the opacities of the eggs, and identifying live eggs of the plurality of eggs using the temperatures of the eggs. The step of identifying live eggs is facilitated by the identification of the clear eggs.

The step of classifying may include identifying a remaining group of the eggs, the remaining group not including the clear eggs, and identifying live eggs in the remaining group using the temperatures of the eggs of the remaining group and not the temperatures of the clear eggs. The method may further include identifying at least one other class of non-live eggs, preferably early dead eggs. The eggs may be physically separated into at least three groups including a live egg group, a clear egg group, and a non-live and non-clear egg group.

According to other embodiments of the present invention, an apparatus for classifying a plurality of poultry eggs each having an opacity and a temperature includes means for detecting the opacities of the eggs, means for detecting the temperatures of the eggs, and means for classifying the eggs using the opacities and the temperatures of the eggs. The means for classifying identifies clear eggs of the plurality of eggs using the opacities of the eggs, and identifies live eggs of the plurality of eggs using the temperatures of the eggs. The identification of live eggs is facilitated by the identification of the clear eggs.

The means for classifying may correct the egg temperatures for relative egg locations using the identification of the clear eggs, and identify live eggs of the plurality of eggs using the corrected egg temperatures. The means for classifying may identify a remaining group of the eggs, the remaining group not including the clear eggs, and identify live eggs in the remaining group using the temperatures of the eggs of the remaining group and not the temperatures of the clear eggs. The means for classifying may identify at least one other class of non-live eggs, preferably early dead eggs. The apparatus may include an injector operative to inject live eggs with a treatment substance.

Preferably, the means for detecting the opacities of the eggs includes a light candling system which detects the opacities of the eggs and generates opacity signals corresponding to the egg opacities, the means for detecting the temperatures of the eggs includes a thermal candling system which detects the temperatures of the eggs and generates temperature signals corresponding to the egg temperatures, and the means for classifying the eggs includes a controller which receives the opacity and temperature signals and classifies the eggs as a function of the opacities and temperatures of the eggs, the controller being operative to selectively generate a control signal based on the egg classifications. The light candling system may comprise an infrared emitter and an infrared detector, and the thermal candling system may comprise an infrared sensor.

According to further embodiments of the present invention, a method for classifying poultry eggs includes providing a plurality of eggs each having a respective physical egg location, measuring the temperatures of the eggs, and classifying the eggs as a function of the temperatures of the eggs. The step of classifying includes determining a spatial temperature trend among the plurality of eggs, and identifying live eggs of the plurality of eggs using the spatial temperature trend.

The step of determining a spatial temperature trend may include generating a temperature trend map including a predicted egg temperature for each egg location. The step of classifying may include correcting the egg temperatures for relative egg locations, and identifying live eggs of the plurality of eggs using the corrected egg temperatures.

Objects of the present invention will be appreciated by those of ordinary skill in the art from a reading of the Figures and the detailed description of the preferred embodiments which follow, such description being merely illustrative of the present invention.

DETAILED DESCRIPTION OF THE PREFERRED EMBODIMENTS

Figure 1:
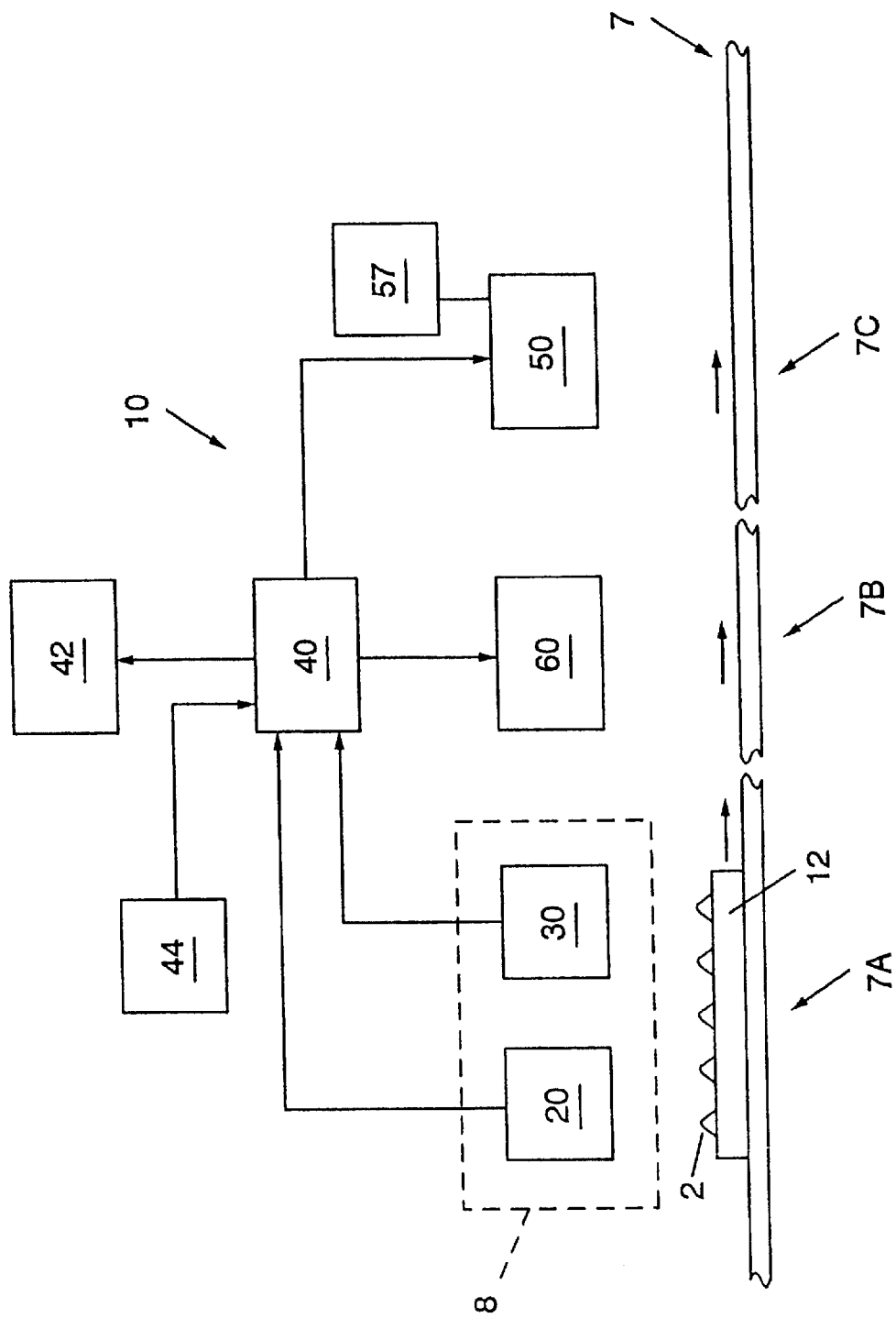
FIG. 1 is a schematic view of an apparatus according to the present invention for selectively classifying, sorting and treating poultry eggs.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention may be carried out with any types of avian eggs, including chicken, turkey, duck, geese, quail, and pheasant eggs. Chicken eggs are particularly preferred.

Typically, eggs are inoculated on or about the eighteenth day of age. At such time, an egg may be one of several commonly recognized types. The egg may be a "live" egg, meaning that it has a viable embryo. The egg may be a "clear" or "infertile" egg, meaning that it does not have an embryo. More particularly, a "clear" egg is an infertile egg that has not rotted. The egg may be an "early dead" egg, meaning that it has an embryo which died at about one to five days old. The egg may be a "mid-dead" egg, meaning that it has an embryo which died at about five to fifteen days old. The egg may be a "late mid-dead" egg, meaning that it has an embryo which died at about fifteen to eighteen days old. The egg may be a "rot" egg, meaning that the egg includes a rotted infertile yolk (for example, as a result of a crack in the egg's shell) or, alternatively, a rotted, dead embryo. While an "early dead", "mid-dead" or "late mid-dead egg" may be a rotted egg, those terms as used herein refer to such eggs which have not rotted. The egg may be an "empty" egg, meaning that a substantial portion of the egg contents are missing, for example, where the egg shell has cracked and the egg material has leaked from the egg. Additionally, from the perspective of many egg detecting and identifying devices, an egg tray may be missing an egg at a particular location, in which case, this location may be termed a "missing" egg. An egg may be placed in an egg tray such that it is an "upside-down" egg, meaning that the egg has been placed in the tray such that the air cell thereof is mislocated, typically with the blunt end down. Clear, early-dead, mid-dead, late mid-dead, and rot eggs may also be categorized as "non-live" eggs because they do not include a living embryo.

Typically, eggs are held in trays on racks in carts for incubation in relatively large incubators. At a selected time, typically on the eighteenth day of age, a cart of eggs is removed from the incubator for the purposes of, ideally, separating out unfit eggs (namely, deads, rots, empties, and clears), inoculating the live eggs and transferring the eggs from the setting flats to the hatching baskets. Certain practical aspects of the incubation, handling and measuring processes may substantially diminish the accuracy of the methods and apparatus for distinguishing between live and dead eggs using thermal candling devices. The temperatures of the eggs may differ based on their relative locations in the incubator because different temperatures or air flows may be present at different locations in the incubator. Also, the thermal environment outside of the incubator may be poorly controlled. As a result, different trays and sections of trays often experience different cooling rates depending on their positions in the cart and exposure to air drafts.

In the candling method and apparatus described in U.S. Pat. No. 4,914,672 to Hebrank, for example, a thermal candling system measures the temperature of each egg from the bottom. The thermal candling system determines a threshold temperature. Eggs above the threshold temperature are deemed live and eggs below the threshold temperature are deemed non-live (which includes dead and clear eggs).

The accuracy of the chosen threshold temperature is jeopardized by non-uniform cooling conditions as discussed above. In order to minimize the risk of improperly identifying a live egg as a non-live egg, the threshold temperature is generally set lower than the predicted temperature of a live egg. Correction factors have been applied to better approximate the appropriate threshold temperatures for different eggs or groups of eggs; however, these correction factors are not as accurate as desired.

While it is disadvantageous to discard live eggs, it is also disadvantageous to retain certain non-live eggs. In particular, if rot or dead eggs are retained and inoculated, the inoculating needle may be contaminated, risking infection of subsequent live, healthy eggs. Furthermore, the treatment substance is wasted if injected in a non-live egg.

Furthermore, in some instances, it may be desirable to identify clear eggs (i.e., infertile, non-rotted eggs) and early dead eggs. While not suitable for producing broilers, these eggs may be useful for commercial food service or low grade food stock (e.g., dog food). The presence of bacterial contamination from rots decreases the value of this food stock.

The present invention is directed to a method and an apparatus for identifying types of eggs which use both a thermal candling system and a light candling system. The light candling system augments the accuracy of the thermal candling system and may identify types of eggs which the thermal candling system may not effectively identify. By use of the inventive method and apparatus, the number of improperly discarded live eggs and the number of inoculated rotted or dead eggs may each be reduced. Additionally, clear and/or early dead eggs may be positively identified and separated from other types of eggs.

According to preferred embodiments, the light candling system is used to identify clear eggs. The thermal candling system is used to distinguish live eggs from non-live eggs using a threshold temperature. The threshold temperature is preferably determined by measuring the temperatures of all or selected ones of the eggs in a tray and deriving therefrom the temperature above which the eggs are expected to be live. The accuracy of this determination is facilitated by use of data collected from the light candling system. In this way, the identification of live eggs versus non-live eggs (i.e., dead, rotted, empty, missing and clear eggs) may be more accurately made, thereby reducing the number of improperly retained rotted or dead eggs which might otherwise contaminate inoculation needles, and minimize the possibility of discarding a live egg.

To further enhance classification accuracy, a spatial temperature trend among the eggs may be determined to account for temperature variations across the flat due to non-uniform micro-environments (for example, resulting from non-uniform air flows in incubators and hallways). Preferably, a temperature trend map for the eggs is generated and used to evaluate the measured egg temperatures. The determination of the threshold temperature may be facilitated by correcting or compensating the measured egg temperatures. Preferably, the amount of correction is determined, at least in part, by considering the temperatures of all eggs except the non-live eggs which have been identified by the light candling system as clear eggs.

According to further preferred embodiments, the eggs are classified by comparing the measured temperatures thereof to corresponding predicted temperatures of a temperature trend map. Preferably, the predicted temperatures are determined, at least in part, by adjusting or excluding the temperatures of the eggs which have been identified as clear eggs by the light candling system.

The determination of a spatial temperature trend may also be used in classifying the eggs without using the light candling data and identification of clears to determine the amount of correction or the predicted temperatures or to otherwise facilitate the classification. Either of the foregoing methods may be modified in this manner.

The eggs which are classified as live may be treated by inoculation with a treatment substance or the like. Because the light candling system identifies clear eggs and early dead eggs, these eggs may be separated from the other non-live eggs for other uses. That is, the non-live eggs may be further classified as clear or early dead and non-clear or early dead. In this way, the light candling system supplements the thermal candling system which may not reliably distinguish between clear or early dead eggs and other non-live eggs. Optionally, the non-live eggs may be further classified as infertiles and early dead or various stages of mid-dead. The classified eggs are then physically separated and transported such that the live eggs are passed on for inoculation or other treatment, the clear eggs (and, optionally, the early dead eggs) are diverted for collection for other uses, and the remaining non-live eggs are discarded.

In the case of upside-down eggs, the light candling system may be used to determine if the egg is clear as opposed to live or dead. Optionally, the thermal candling system may include sensors for measuring the temperatures at each end of an upside-down egg to determine whether the egg is live or non-live.

The light candling system may be used to further estimate the quantities or statistics of early mid-dead, mid-dead, late mid-dead, rot and empty eggs. Such information may be desired for the purposes of evaluating groups of eggs.

Turning to the preferred embodiments of the method and the apparatus in greater detail, said method and apparatus identify, classify, report, sort, and inoculate or otherwise treat eggs of a group of eggs. It will be appreciated that various aspects and features of the method and apparatus may be omitted or used separately from the described method and apparatus. The method and apparatus employ both a thermal candling system and a light candling system to identify each or selected ones of the eggs. A controller of the apparatus collects data regarding the eggs from the thermal candling system and the light candling system, classifies the eggs, and sorts or treats the eggs in accordance with their classifications and pre-determined standards or parameters.

With reference to FIG. 1, an apparatus 10 according to the present invention is shown schematically therein. The apparatus 10 is used to sort and treat a plurality of eggs 2 which are preferably provided in a flat 12. The apparatus 10 includes an identification or candling station 8 (hereinafter, "the candling station 8"). The candling station 8 in turn includes a light candling system 20 and a thermal candling system 30. The light candling system 20 and the thermal candling system 30 each serve to assess various characteristics of the eggs which may be used to evaluate and classify the eggs.

The light candling system 20 and the thermal candling system 30 are operatively connected to a controller 40. The controller 40 controls the candling station 8 and receives and processes signals from the candling station 8. The controller 40 also collects and analyzes data regarding each or selected ones of the eggs from the candling station 8 and, using this data, classifies the eggs as to type. A display 42 and a user controlled interface 44 are provided to allow the operator to interact with the controller 40.

A sorting station 60 may be provided downstream of the candling station 8. As discussed below, the controller 40 generates a selective removal signal based on the presence and relative position of each suitable egg to cause the sorting station 60 to remove prescribed classes of eggs. The prescribed classes preferably include clear eggs and may also include other non-live eggs.

A treatment station 50 is provided downstream of the candling system 8. As discussed below, the controller 40 generates a selective treatment signal based on the presence and relative position of each suitable egg to cause the treatment station 50 to treat, for example, by inoculation with a treatment substance, prescribed classes of eggs.

A conveying system 7 serves to transport the eggs through and, optionally, between, each of the stations 8, 50, and 60. The conveying system 7 includes conveyors 7A, 7B and 7C associated with the stations 8, 60 and 50, respectively. The conveyors 7A, 7B, 7C may be separate conveyors or a continuously configured conveyor.

With reference to FIGS. 2–5, the candling station 8 and the associated conveyor 7A are shown therein. As discussed above, the candling system 8 includes the light candling system 20 and the thermal candling system 30. The conveyor 7A transports the flat 12 of eggs 2 by each of the light candling system 20 and the thermal candling system 30.

The light candling system 20 is preferably a light candling system as described in U.S. Pat. No. 5,745,228 to Hebrank et al., which is hereby incorporated herein by reference in its entirety, wherein light is pulsed at a frequency different from (and preferably higher than) ambient light. Suitable light candling systems include the light candling system forming a part of the Vaccine Saver™ vaccine delivery system available from Embrex, Inc. of Research Triangle Park, N.C. with suitable modifications. In overview, the light candling system of U.S. Pat. No. 5,745,228 comprises a photodetector associated with a photodetector amplifier and filter circuit, which is in turn associated with a PC analog input board, and a photoemitter (an infrared emitter) associated with an IR emitter driver circuit, in turn associated with a digital output board. The photoemitter and photodetector are positioned to be on opposite sides of an egg, preferably with the photodetector above and the photoemitter below the egg, but these positions are not critical and could be reversed, or the emitter and detector placed in a different orientation, so long as light from the emitter illuminates the egg to the detector. The input and output boards may be installed in a personal computer, with operation of the system monitored on the display screen of the PC computer.

In operation, the light candling system 20 uses time to allow accurate measurement of the light from a single egg. Light is generated in short bursts from each photoemitter (e.g., 50 to 300 microseconds) and the corresponding photodetector only monitors while its corresponding photoemitter is operational. To reduce the effect of ambient light, the output of a photodetector when no light is on is subtracted from the reading when the light is on. Preferably, light is generated in a short burst from a photoemitter, and the corresponding photodetector monitors the light level immediately before, during, and immediately after the burst of light is generated. A flat of eggs is continuously "scanned" as it moves through the identifier with each detector-source pair active only while at least adjacent, and preferably all other, pairs are quiescent.

Turning to the construction of the light candling system 20 in more detail and with reference to FIGS. 2–5, the light candling system 20 includes an infrared light emitter mounting block 11 and an infrared light detector mounting block 21 mounted on the conveyor 7A. The infrared light emitter mounting block 11 is comprised of an opaque black plate 16 with the infrared emitters 17 (Photonics Detectors, Inc. Part number PDI-E805) mounted thereto. These emitters include an integral lens, but a nonintegral lens system could also be provided for the emitter. These gallium-arsenide light-emitting diodes emit infrared light with a wavelength of 880 nanometers and can be switched on or off with activation times of about one microsecond. An opaque polymer block 18 that is 0.5 inches thick has ¼ inch diameter holes 18A bored therethrough in corresponding relation to each emitter. A 0.040" polycarbonate sheet 19 (opaque except for a 0.25 inch circle above each emitter) overlies the block 18. The structure of the mounting block thus provides an optical aperture positioned between the egg and the light emitters 17. In one embodiment, sheets available commercially for overhead projector transparencies are used.

Likewise, the infrared light detector mounting block 21 is comprised of an opaque back plate 26 with the infrared detectors 27 (Texas Instruments Part number TSL261) mounted thereto. Integral lenses or non-integral lens systems could optionally be provided with the detectors. An opaque polymer block 28 that is 0.5 inches thick has ¾ inch diameter holes 28A bored therethrough in corresponding relation to each emitter. A 0.040 inch polycarbonate sheet 29 (opaque except for a 0.25 inch circle above each detector) overlies the block 28. The polycarbonate sheets may be a light-blocking, infrared transmissive polymer that have about 90% transmittance of wavelengths between 750 and 2000 nanometers. The infrared light from the emitters has a wavelength near 880 nanometers. Thus, the sheets serve, at least in part, to block and filter ambient light. Again, the structure of the mounting block thus provides an optical aperture positioned between the egg and the light detectors 27.

In all cases, opaque materials are preferably black. The apparatus is configured so that the distance "a" from the top of the egg to the polymer film 29 is from ½ to one inch, and so that the distance "b" from the bottom of the egg to the polymer film 19 is from ½ to one inch, with a distance of 0.5 inches preferred. Note that some egg flats and the variety of egg sizes cause this distance to typically range from ⅜ inch to one inch. The size of the viewed area on the egg is typically from about 0.1 inches to about 0.3 inches in diameter. Smaller areas typically give better rejection of light reflected off of adjacent eggs.

A switching circuit is operatively associated with the light source for cycling the intensity of the light from the emitters 17 at a frequency greater than 100 cycles per second, and preferably at a frequency greater than 200 or 400 cycles per second. An electronic filter is operatively associated with the light detectors 27 and is configured to distinguish light emitted from the light source from ambient light (i.e., by filtering out higher and/or lower frequency light signals detected by the detector). All may be conventional circuitry, and numerous variations thereon will be readily apparent to those skilled in the art.

In operation, each emitter 17 is typically turned on for about 250 microseconds. The output of each photodetector 27 is amplified by a bandwidth-limited filter (2 kHz low pass filter combined with a 1.0 kHz high pass filter). The filter maximizes detection of the 250 microsecond pulses of light from the photoemitters while minimizing noise from either electronic circuitry or stray light in the environment. The output from each filter is sampled about 120 microseconds after the corresponding emitter is turned on. The samples are digitized and recorded by the computer. A second sample is taken about 250 microseconds after the corresponding emitter is turned off. The off-light sample when subtracted from the on-light sample further improves rejection of ambient lighting around the identifier.

In another embodiment of the light emitter mounting block 11, the diodes are mounted in an opaque polymer block 18 that positions the diodes and protects them from water and dust in the working environment. A flat sapphire window above each diode is transparent to the light from the diode. Similarly, the light detector mounting block 21 may be comprised of an opaque back plate 26 with lensed infrared detectors (IPL Part number IPL10530DAL) mounted thereto. An opaque polymer block 28 that is 0.6 inches thick has 0.33 inch diameter holes bored therethrough in corresponding relation to each emitter. A transparent sapphire window allows light passing through an egg to illuminate the detector above it. Some of the photoemitters may be slightly off set from the center line of the eggs so that they miss the conveyor belts.

In another embodiment, in the operation of an apparatus as described above, each emitter is typically turned on for about 70 microseconds. The output from each detector is sampled just before and about 70 microseconds after the corresponding emitter is turned on. A third sample is taken about 70 microseconds after the corresponding emitter is turned off. The samples are digitized and recorded by the computer. The off-light samples are averaged and subtracted from the on-light sample to improve rejection of ambient lighting around the identifier.

While preferred light candling systems have been described, any other suitable device for measuring the opacities of eggs may be used in the method and apparatus of the present invention. Such other suitable devices will be apparent to those of skilled in the art from upon reading the description herein.

The controller 40 is operatively connected to and actuates the infrared emitters 17 to pulse light at a frequency different than (and preferably higher than) the ambient light as described above. A portion of the light from the emitters 17 is transmitted through the eggs 2 and received by the corresponding detectors 27. The controller 40 is operatively connected to and receives signals generated by each detector 27 corresponding to the light level (or irradiance) of the glowing egg and the resulting intensity of the light incident at the detector 27. In this manner, the controller is provided by the light candling system 20 with assessments of the respective opacities of the eggs. It is not necessary that the detectors 27 be collinearly aligned with their associated emitters 17 because the light entering the eggs is diffused by the shells and contents of the eggs.

The thermal candling system 30 is preferably a thermal candling system as described in U.S. Pat. No. 4,914,672 and in U.S. Pat. No. 4,955,728, each to Hebrank, each of which are hereby incorporated herein in their entireties. The thermal candling system 30 includes a mounting bracket 31 and a plurality of infrared thermal sensors 37 mounted therein at locations corresponding to each egg 2 in a row of the flat 12. The thermal sensors 37 are operative to measure the infrared radiation emitted by each egg passed thereby. The controller 40 is operatively connected to each of the infrared thermal sensors 37 to receive signals from the sensor 37 corresponding to the temperature at the sensor 37. Means associated with either the sensors 37 or the controller 40 convert the infrared radiation measurement to a corresponding temperature value, typically using a standard algorithm and calibration data. The sensors 37 may be infrared thermometers which produce an output signal in degrees Celsius or Fahrenheit and require no further conversion. As an alternative, the temperature measurements may be made by contact temperature sensors (not shown) such as thermistors or thermocouples which are placed against sides or non-air cell ends of the eggs or by an infrared video camera.

As used herein, the designation "infrared radiation" refers to electromagnetic radiation having a wavelength of between about 2.5 and about 50 microns (or expressed differently, that having a frequency of between about 200 and about 4000 inverse centimeters $cm^{-1}$ or "wave numbers"). As understood by those familiar with infrared (IR) radiation and the IR spectrum, the frequencies of electromagnetic radiation generally characterized as infrared are emitted or absorbed by vibrating molecules, and such vibrations generally correspond to the thermal state of a material in relation to its surroundings. All solid bodies whose temperatures are above absolute zero radiate some infrared energy, and for temperatures up to about 3500 K (3227° Celsius, 5840° Fahrenheit), such thermal radiation falls predominately within the infrared portion of the electromagnetic spectrum. There thus exists a rather straightforward relationship between the temperature of a body and the infrared radiation which it emits. In the present invention, the monitoring of radiation in the range of 8–14 microns is currently preferred.

As further understood by those familiar with electromagnetic radiation, however, wavelengths below 2.5 microns (usually 0.8 to 2.5 microns or 4000–12,500 $cm^{-1}$) are also considered as the "near IR" portion of the electromagnetic spectrum, and represent vibrational "overtones" and low level electronic transitions. Similarly, wavelengths above 50 microns (usually 50 to about 1000 microns or 10–200 $cm^{-1}$) are considered to be "far IR" portion of the electromagnetic spectrum and represent energy associated with molecular rotations.

It will thus be understood that the designation "infrared" is used in a descriptive rather than a limiting sense and that measurement of thermal radiation from eggs which falls outside of these particular frequencies is encompassed by the scope of the present invention.

Optionally, the thermal candling system 30 may include thermal sensors 37 positioned to detect the temperature at both ends of each egg. In this manner, an accurate reading of the temperatures of eggs positioned upside-down in the flat may be made. The controller 40 should be programmed to recognize the presence of an upside-down egg from the temperature differential between the associated, opposed thermal sensors 37, and to classify the egg according to the temperature measured at the non-air cell end. Further, the controller 40 may be operative to report the presence and location of the upside-down egg via the display 44.

Preferably, the eggs are carried in egg flats 12 as described herein; however, as will be apparent to those ordinarily skilled in the art, any means of presenting a plurality of eggs over time to the candling station 8 for identification of suitable eggs can be used in the present methods. The eggs may pass one at a time under the candling station 8 or, as described herein, the candling station 8 may be configured so that a number of eggs can pass under the candling station 8 simultaneously.

Figure 2:
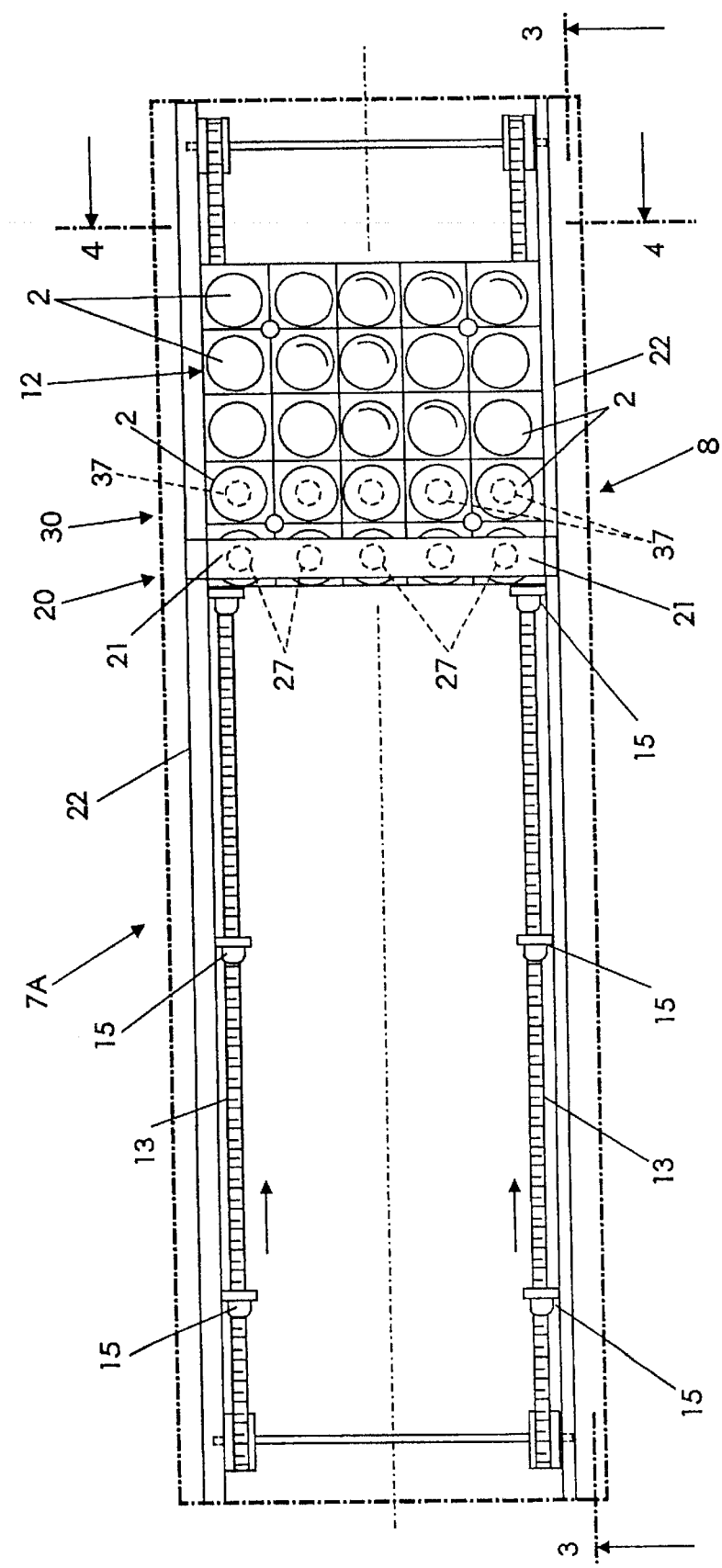
FIG. 2 is a top view of a flat of eggs in a candling station of the apparatus of FIG. 1.
Figure 3:
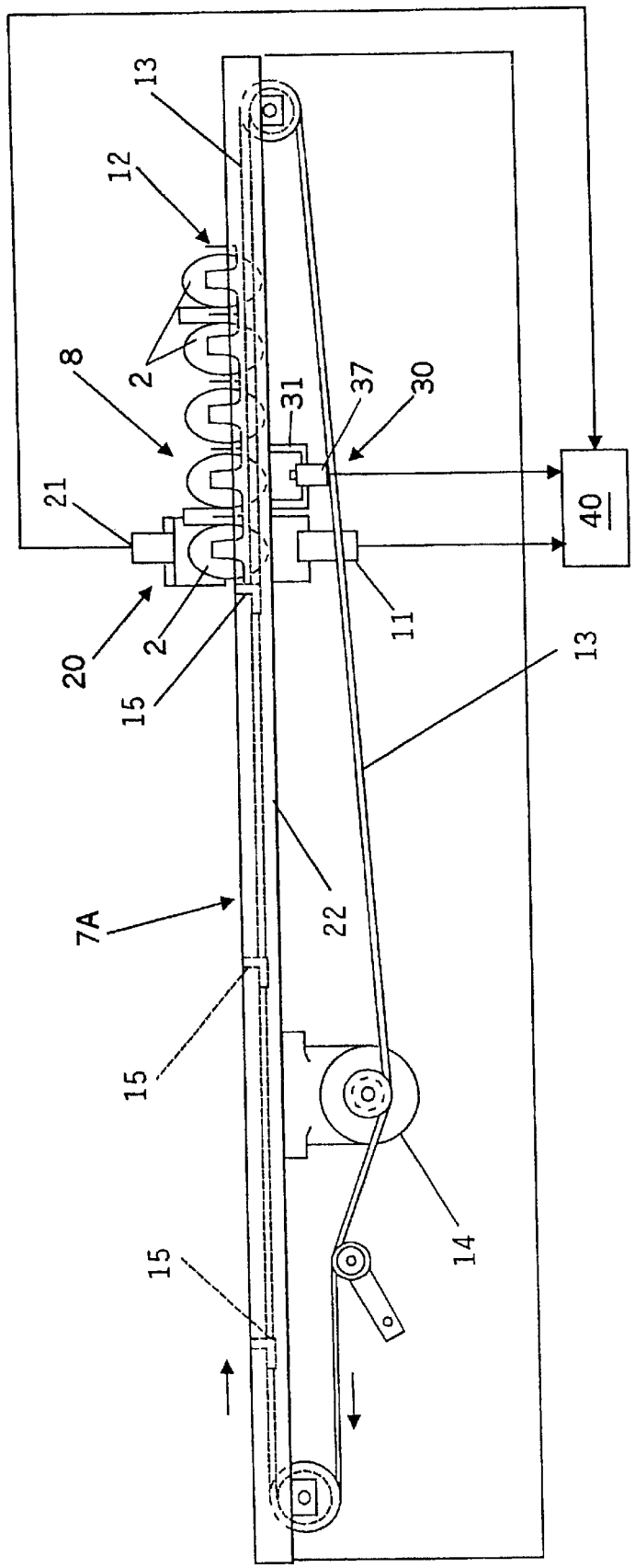
FIG. 3 is a side elevational view taken along the line 3—3 of FIG. 2.
Figure 4:
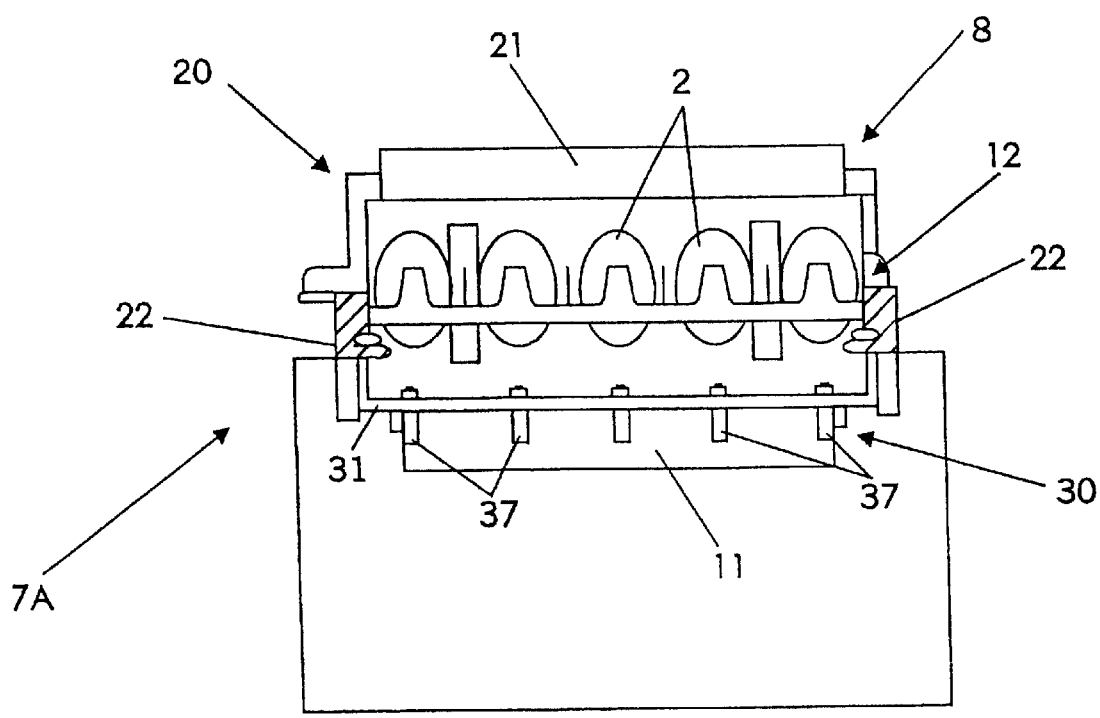
FIG. 4 is an end elevational view taken along the line 4—4 of FIG. 2.
Figure 5:
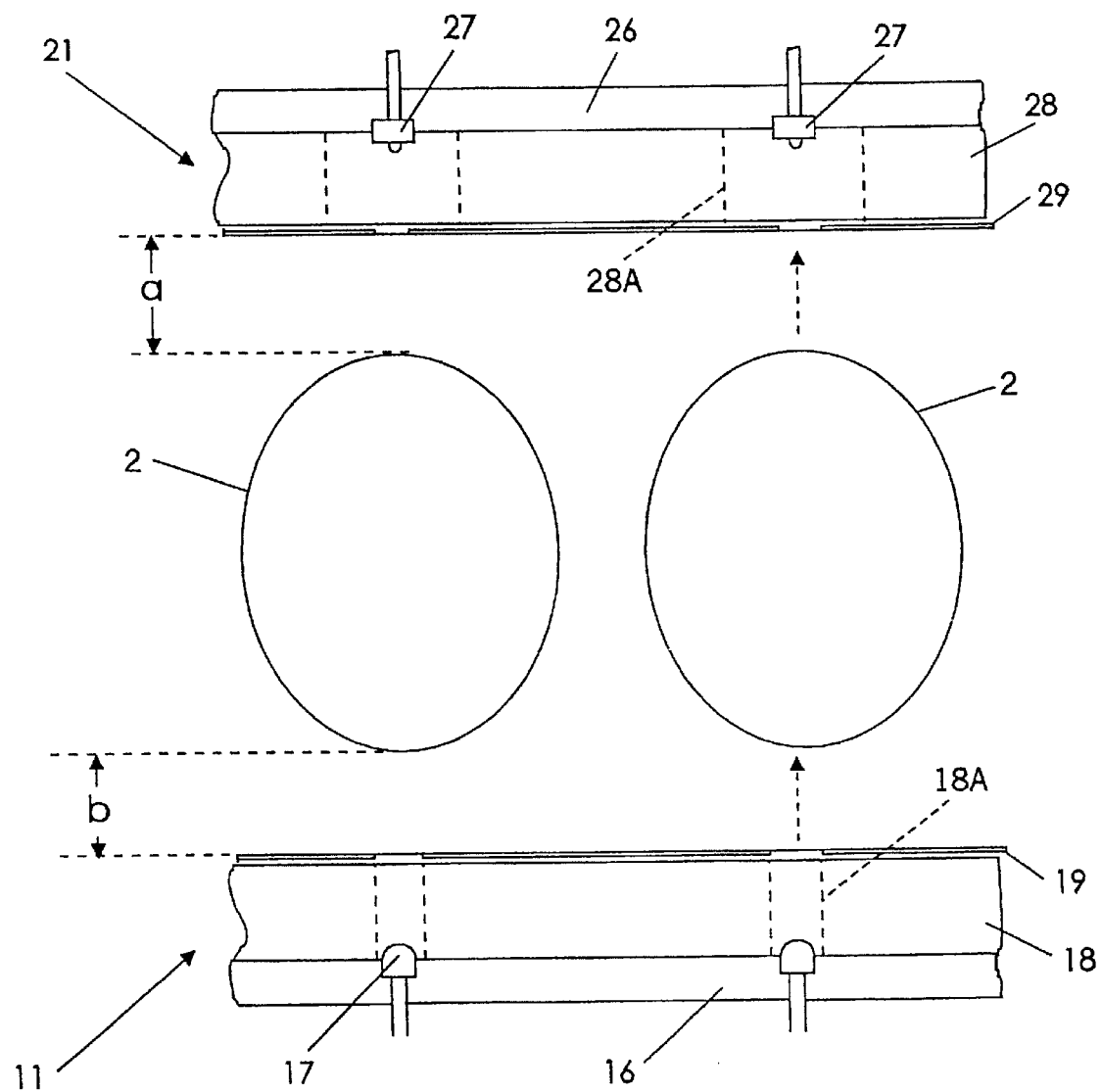
FIG. 5 is a detailed view of a light source mounting block and a light detector mounting block of the apparatus of FIG. 1.

Any flat of eggs with rows of eggs therein may be used, and while five rows are illustrated in the flat 12 shown schematically in FIG. 2, the flat may contain any number of rows, such as seven rows of eggs, with rows of six and seven being most common. Eggs in adjacent rows may be parallel to one another, as in a "rectangular" flat, or may be in a staggered relationship, as in an "offset" flat (not shown). Examples of suitable commercial flats include, but are not limited to, the "CHICKMASTER 54" flat, the "JAMESWAY 42" flat and the "JAMESWAY 84" flat (in each case, the number indicates the number of eggs carried by the flat). As illustrated in FIGS. 2 and 3, the flat 12 is an open bottom setting flat and carries twenty-five eggs in a fixed array of five rows of five eggs each.

The flat 12 rides on the conveyor 7A. As shown, the conveyor 7A includes drive chains 13, chain drive motor 14 and chain drive dogs 15 that move the flat along the guide rails 22 adjacent the path of the chain 13. In an alternate, preferred embodiment, the chain drive and dogs are replaced with a pair of polymeric conveyor belts riding on support rails, which conveyor belts are ⅜ inch diameter and ride on 0.5 inch frames. Such belts are as found on egg injection equipment, particularly the EMBREX INOVOJECT® egg injection apparatus, and are desirable for their comparability with operator safety and corrosion resistance. Egg flats are typically moved at rates of 10 to 20 inches per second. The eggs are preferably placed in the flat such that the air cell ends thereof do not pass adjacent the thermal sensors 37.

As discussed above, the infrared emitters 17, the infrared detectors 27 and the infrared thermal sensors 37 are each operatively connected to the controller 40. The controller 40 includes processing means which: 1) generate control signals to actuate and deactuate the emitters 17; 2) receive and process the signals from the detectors 27 and the sensors 37; 3) process and store data associated with each egg; and 4) generate control signals to operate the treatment station 50 and the sorting station 60. The controller 40 preferably includes a PC having a microprocessor or other suitable programmable or non-programmable circuitry including suitable software. The controller 40 may also include such other devices as appropriate to drive the emitters 17 and receive, process or otherwise assess and evaluate signals from the detectors 27 and the sensors 37. Suitable devices, circuitry and software will be readily apparent to those of ordinary skill in the art upon reading the foregoing and following descriptions and the disclosures of U.S. Pat. Nos. 5,745,228 to Hebrank et al. and U.S. Pat. No. 4,955,728 to Hebrank. The processing computer and other devices may be housed in a common cabinet or separate cabinets.

The operator interface 44 may be any suitable user interface device and preferably includes a touch screen or keyboard. The operator interface 44 may allow the user to retrieve various information from the controller 40, to set various parameters and/or to program/reprogram the controller 40. The operator interface 44 may include other peripheral devices, for example, a printer and a connection to a computer network.

Figure 6:
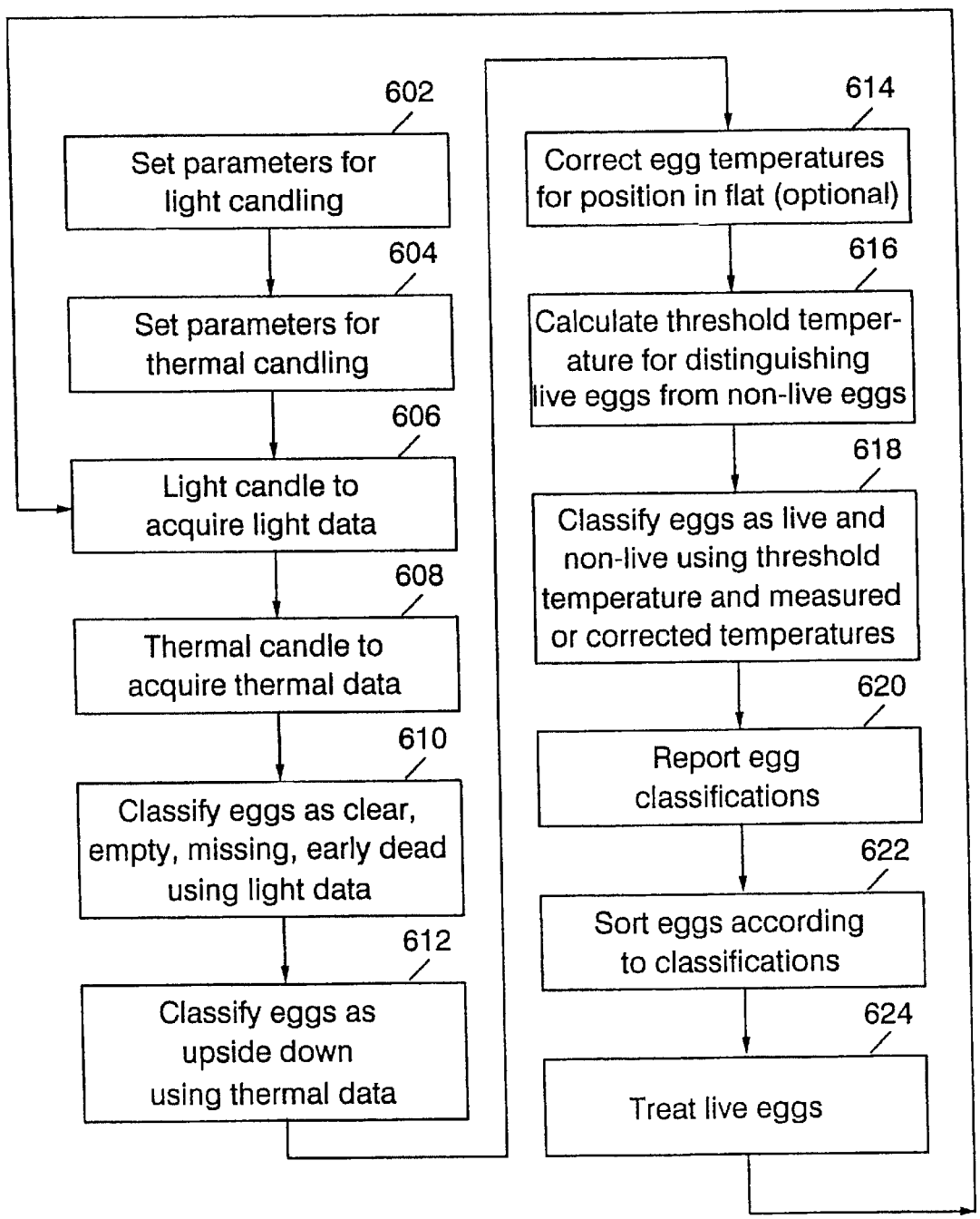
FIG. 6 is a flow chart representing a method according to the present invention for selectively classifying, sorting and treating poultry eggs.

With reference to FIG. 6, the eggs may be assessed, classified, sorted, treated and reported using the above described apparatus and the following method. The method is premised on the discovery that regardless of thermal surroundings, non-live eggs, and in particular, clear eggs, tend to be cooler than live eggs under those same conditions. Because thermal surroundings and thermal history affect the absolute temperatures of both live and non-live eggs, measurement of one egg's individual temperature or cooling rate, standing alone, may not provide sufficient information to determine whether the egg is live or non-live.

The individual egg temperatures are monitored and used to determine a threshold egg temperature for the selected group of eggs, it being understood that, as used herein, the term "threshold" means the computation of a relative standard temperature for the group against which the temperatures of the individual eggs can be compared, and which provides a threshold for determining whether any given egg is live or non-live. The threshold temperature is determined, at least in part, by evaluating the temperatures of those eggs identified as clear eggs.

Once the threshold temperature has been determined, the next step in the method of the invention is the determination of the difference between each individual egg temperature and the threshold temperature of the selected group, following which the resulting status of each egg may be determined. The classified eggs may thereafter be reported, sorted and treated as appropriate.

Turning to the method in more detail, initially, certain parameters or thresholds are set (Block 602). These parameters may set the desired margins for error reflective of the determined or expected costs of mis-classifying live eggs, clear eggs or rot eggs. The desired thresholds for the light intensities incident at the detectors 27, including any variances, are set. Some or all of the thresholds may be set by the operator or may be fixed or preset thresholds. Some or all of the thresholds may also be operator set but automatically modified by the controller 40 based on other conditions such as measured ambient light, average light levels for clears, or average light levels for lives. The light intensities incident at the detector 27 will be inversely proportional to the opacities of the respective eggs 2. That is, more opaque eggs will transmit less of the light from the associated emitters 17, thereby reducing the intensity of the light at the associated detectors 27 corresponding amounts. The thresholds preferably include threshold values $L_e$, $L_c$, $L_{md}$ and $L_f$, which are related as follows:

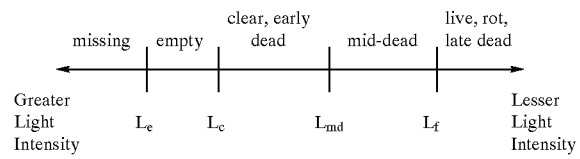

where:
(1) above the $L_e$, the egg slot will be considered empty;
(2) between $L_e$ and $L_c$, the egg will be considered empty;
(3) between $L_c$ and $L_{md}$, the egg will be considered clear or early dead;
(4) between $L_{md}$ and $L_f$, the egg will be considered mid-dead; and
(5) below $L_f$, the egg will be considered fertile or rotted, but not clear, early dead or mid-dead.

Additional thresholds may be used as well. For example, thresholds may be set which distinguish between clear and early dead or early mid-dead and late mid-dead. Also, one or more thresholds may be omitted. For example, the $L_{md}$ threshold may serve as the $L_f$ threshold such that an egg for which the light intensity at the associated detector 27 is less than $L_{md}$ will be considered mid-dead, live, rot or late dead, and intensities greater than $L_{md}$ but less than $L_c$ will be considered clears and early deads.

Certain temperature related values may also be set (Block 604). For example, standard deviations for egg temperatures may be set by an operator or may be fixed or preset. The threshold temperatures may also be automatically modified by the controller 40 based on other conditions such as coefficient of variation of the clear eggs or the live eggs. The controller may be provided with a program including an algorithm and/or look up table for determining the threshold temperatures from the measured live and clear egg temperatures.

The flat 12 of eggs 2 is placed on the conveyor 7A which transports the flat to the light candling system 20. Preferably, the front edge of an egg flat 12 is located either by the flat 12 moving up to a fixed stop (not shown) or by a photo-optic device (not shown), also operatively associated with the computer, locating the front edge of the flat. Normally the rows of emitters 17 and detectors 27 are aligned with the front row of the flat 12 at that time. The flat 12 is then moved forward by the conveyor system 7A while the row of detectors 27 continuously scan the eggs. Software associated with the controller 40 defines the passage of rows of eggs 2 by the strong light that passes between the eggs 2 as the margin between rows moves past the detectors. As a check on the location of rows, the computer may also monitor the running or stopped state of the conveyor motor.

Row by row, the conveyor 7A passes the eggs by the emitters 17 and detectors 27, and the light candling system 20 measures the opacity of each egg or selected eggs and generates corresponding signals to the controller 40 (Block 606). The controller 40 processes, indexes and stores this data for each assessed egg thereby generating an opacity or light candling data set.

The flat of eggs is also transported by the conveyor 7A through the thermal candling system 30, before, after (as shown), or simultaneously with the light candling step. The thermal candling system 30 measures the temperature (or the corresponding infrared radiation) of each egg and generates corresponding signals to the controller 40 (Block 608). The controller 40 processes, indexes and stores this data for each egg, thereby generating a temperature or thermal candling data set. Row detection data from the light identifier may be used to index the conveyor or signal when an egg's position is over the thermal sensor for improved accuracy of the thermal candler.

It will be appreciated that, following the steps of assessing the opacity of each or certain eggs (by light candling) and assessing the temperature of each egg (by thermal candling), the controller 40 will have a temperature profile for each assessed egg and an opacity profile for all or certain eggs. The controller 40 evaluates each egg profile by comparing the data to the preset threshold values. According to a preferred method, the controller 40 first evaluates the eggs using the light candling data and then evaluates the eggs using the thermal candling data in view of the light candling data.

More particularly, the controller 40 compares the light candling data for each assessed egg to the threshold light intensities $L_e$, $L_c$, $L_{md}$, and $L_f$ and classifies the eggs in accordance therewith (Block 610). If, for a given egg, the light intensity exceeds $L_e$, the egg is classified as an empty slot in the flat 12 (i.e., missing). If the light intensity is between $L_e$ and $L_c$, the egg is classified as an empty egg. If the light intensity is between $L_c$ and $L_{md}$, the egg is classified as a clear/early dead egg. If the light intensity is between $L_{md}$ and $L_f$, the egg is classified as a mid-dead egg. Additionally, the preferred light candling system as described above allows resolution of the age of the mid-dead eggs by the shape and intensity of the one-dimensional image of egg transparency. If the light intensity is less than $L_f$, the egg is classified as fertile or rotted, but not clear, early dead or mid-dead.

The controller 40 then uses the classifications of the eggs from the light candling data to determine the appropriate threshold temperature (Block 616) and, optionally, to correct or compensate the temperature values as measured by the thermal candling system 30 (Block 614). As discussed hereinafter, this may be accomplished by different methods.

According to a preferred method ("Method A"), temperatures of all eggs classified by the light candling system as clear, early dead or mid-dead are used to calculate an "average non-live temperature" (ANLT) by arithmetic averaging of the temperatures in this group. Any egg more than a prescribed amount (e.g., 5° F.) cooler than the ANLT is considered to be upside-down (Block 612). If a second set of thermal detectors is provided, the differentials between the temperature values at either end of each egg may be used to identify and classify upside-down eggs (Block 612). If there are few or no non-live eggs on a flat, then upside-down eggs are identified as more than a prescribed temperature amount, for example, seven degrees, cooler than the average of all non-clear, non-mid-dead eggs on a flat. Alternatively, upside-down eggs may be identified as those eggs having a measured temperature more than a prescribed temperature amount, for example, five degrees, cooler than the warmest measured egg temperature.

The remaining eggs (i.e., those eggs not classified as clear, early dead, mid-dead or upside-down) that are warmer than the ANLT are used to calculate an "average live temperature" (ALT) and a "live egg standard deviation" (LESD) by calculating the average and standard deviation of the measured temperature of these eggs. The "threshold temperature" (TT) that is used to distinguish live from non-live eggs is preferably typically set halfway between the ANLT and the ALT. However, if the LESD is larger than a predetermined value, then the threshold temperature (TT) should be set to a value closer to the ANLT to lessen the possibility that a live egg is discarded. If a flat has very few or no clear or mid-dead eggs, then the threshold temperature is set by subtracting a temperature increment from the ALT. This increment is a preset value or based upon data from previous flats. The threshold temperature (TT) is calculated according to the formula:

$$TT = k*(ALT - ANLT) + ANLT,$$

where k is preferably set between 0.1 and 0.5. For LESD's at or below the predetermined value, k is preferably set at 0.5. For LESD's greater than the predetermined value, k should be reduced. The operator can enter values of k or k can be automatically set from a lookup table that gives k as a function of LESD. The predetermined LESD value may be set by the operator or may be automatically set.

Preferably, the egg temperatures are corrected or compensated for position of the egg in the flat to improve classification accuracy (Block 614). For example, in a hatchery hallway with cool, moving air, eggs on an outside row of a flat will cool more quickly and be cooler than eggs located near the center of the flat. The individual egg temperatures are corrected, preferably in the manner described below, to determine corrected egg temperatures. The corrected or compensated egg temperatures are used in place of the measured egg temperatures to calculate the ALT, the ANLT and the threshold temperature (TT). The corrected egg temperatures are also used in place of the measured egg temperatures for comparing to the threshold temperature to distinguish live from non-live eggs. In order that the upside-down eggs may be identified to remove them from the correction procedure, an ANLT is preferably calculated using the measured, uncorrected temperatures; and the uncorrected temperatures are compared to this ANLT to identify the upside-down eggs.

According to some preferred embodiments, the temperature correction is performed using only those eggs that have not been determined by the light candling to be clears. More preferably, the upside-down eggs are excluded as well. Most preferably, the temperature correction or compensation is performed using only "probable lives and rots" (PLR), that is, those eggs that light candling has determined are not clear, early dead, empty or mid-dead, and that thermal candling (using the measured, uncorrected temperatures) has determined are not upside-down.

Temperature correction or compensation is accomplished by establishing the temperature trend across the flat of eggs among the selected eggs (e.g., the non-clears or PLR's) caused by variations in the thermal environment, and then normalizing all of the eggs for this trend (hereinafter "predicted temperatures"). These predicted temperatures form a Temperature Trend Map (TTM). The predicted temperatures may be expressed by the two-dimensional, second-order, least squares fit equation:

$$T_{Predicted}(i,j) = (c1*i^2) + (c2*i) + (c3*j^2) + (c4*j) + c5$$

where:

$T_{Predicted}(i,j)$ is the predicted temperature for an egg located at position i and j, for example, in a row i and an intersecting column j; and c1 to c5 are constants calculated by minimizing the sum of the squares of the differences between the predicted and measured temperatures for each selected egg.

After calculating the predicted temperature, the "corrected (or compensated) temperature" for each egg is calculated by subtracting from the measured temperature of the egg the amount the predicted temperature for the egg exceeds the average flat temperature. That is:

$$T_{Corrected}(i,j) = T_{Measured}(i,j) - [T_{Predicted}(i,j) - T_{Average\ for\ the\ flat}]$$

where $T_{average\ for\ the\ flat}$ is the simple average of the temperatures of all eggs used in the calculation of the predicted temperature equation.

Temperature corrections or compensations for non-uniform thermal environments are typically more accurate if the difference in temperatures between live and non-live eggs is not allowed to affect the correction. Typically, 70% to 90% of the eggs on a flat are live, 5% to 25% are clears and early deads, and less than 5% are malpositions (e.g., upside-down), mid-deads and rots. By eliminating malpositioned, clear and early dead eggs from the calculation of the predicted temperature, most of the live/dead temperature variation is removed from the predicted temperature. In other words, by eliminating most of the non-live eggs from the calculations, the predicted temperatures are more accurate and less influenced by groupings of non-live eggs which may skew the predicted temperatures in an area of the flat. The individual corrected egg temperatures for all of the eggs (live and non-live) are used in place of the measured egg temperatures to calculate the average live temperature (ALT) and the average non-live temperature (ANLT) in the manner described above. Accordingly, the calculated threshold temperature (TT) reflects the correction procedure applied to all of the eggs of the flat.

After correcting or compensating the egg temperatures according to location, a threshold temperature can be calculated and classifications of the eggs as live versus non-live may be made by comparing the individual corrected egg temperatures to the threshold temperature (Block 618). Eggs having temperatures equal to or exceeding the threshold temperature are classified as live, all other eggs are classified as non-live. The LESD may be referenced to affirm that the correction of the egg temperatures was accurate.

Figure 12:
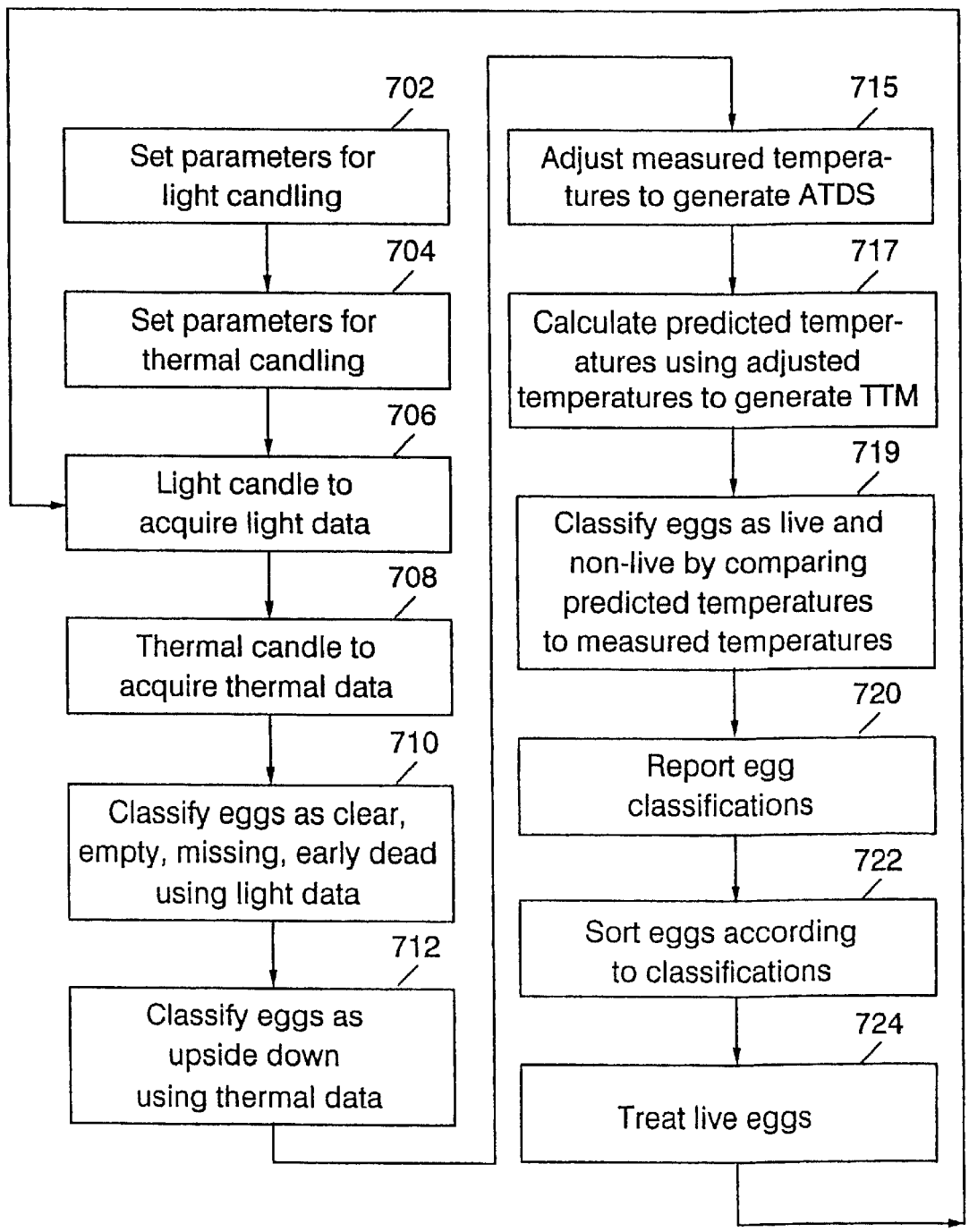
FIG. 12 is a flow chart representing a further method according to the present invention for selectively classifying, sorting and treating poultry eggs.

Alternatively, and with reference to FIG. 12, the eggs may be classified by the following procedure ("Method B"), which also includes establishing a spatial temperature trend among the eggs on the flat. Blocks 702–724 correspond to Blocks 602–624 except that the steps of Blocks 614, 616 and 618 are replaced by the steps of Blocks 715, 717 and 719. A measured temperature ($T_{Measured}(i,j)$) is obtained for each egg by thermal candling. The clear eggs are identified using the light candling data and the upside-down eggs are identified using the thermal candling data in the manners described above. The light candling data may also be used to identify early dead, empty and/or mid-dead-eggs. If early dead and/or mid-dead eggs are identified by light candling with sufficient confidence, they will be treated in the same manner as clear eggs for the remainder of the procedure and the use of the term "clear eggs" should be understood to include such eggs.

The controller generates an Adjusted Temperature Data Set (ATDS) (Block 715) comprising an adjusted temperature ($T_{adj}(i,j)$) for each egg that is not upside-down or empty, and wherein:

1. For eggs identified as clear eggs (and, if identified, early dead and mid-dead eggs):

$$T_{adj}(i,j) = T_{Measured}(i,j) + X \text{ degrees}$$

X may be a constant or a calculated value. If X is a constant, it is preferably about 2° F. X degrees represents the expected temperature difference between a live egg and a clear egg under the same conditions (i.e., in the same micro-environment).

2. The temperatures of empty and upside-down eggs are excluded as if they were empty slots in the flat (i.e., missing eggs).

3. For the remaining eggs:

$$T_{adj}(i,j) = T_{Measured}(i,j)$$

If any early dead and/or mid-dead eggs are not identified as such using the light candling data, they will be included in the remaining eggs set by default.

Thereafter, a Temperature Trend Map (TTM) is generated for the flat using the ATDS. Preferably, the TTM may be expressed as an equation or equation set for which a predicted temperature ($T_{Predicted}(i,j)$) may be determined for each egg location (i,j) (Block 717). More preferably, the TTM is generated using a two-dimensional, second order, least squares fit such that:

$$T_{Predicted}(i,j) = (c1*i^2) + (c2*i) + (c3*j^2) + (c4*j) + c5$$

where:

c1 to c5 are constants calculated by minimizing the sum of the squares of the differences between the predicted and adjusted temperatures for each selected egg.

$T_{Predicted}(i,j)$ represents the expected temperature of an egg located at position i and j (for example, in a row i and an intersecting column j) if the temperature of that egg follows the trend.

The measured temperature ($T_{Measured}(i,j)$) for each egg is then compared to the predicted temperature ($T_{Predicted}(i,j)$) for an egg at that location (Block 719). Typically, the majority of the eggs (for example, 70–90%) in a given flat will be live, in which case the $T_{Predicted}(i,j)$ will be relatively close to the expected temperature of a live egg. However, because the TTM may reflect the presence of some non-live, non-clear eggs, the $T_{Predicted}(i,j)$ for an egg at a given location may be expected to be somewhat less than the expected $T_{Measured}(i,j)$ of a live egg at the same location in view of the temperature trend analysis. Because a second-order fit may not follow the exact temperature distribution, errors may cause predicted live temperatures to vary above and below live egg temperatures. Notably, because the temperatures of most of the non-live eggs (for example, the clear eggs and any other non-live eggs identified by light candling) are adjusted for use in generating the TTM, the tendency for the presence of the clear eggs or other non-live eggs identified by light candling in the flat to skew the $T_{Predicted}(i,j)$ away from the expected $T_{Measured}(i,j)$ of a live egg is minimized.

In view of the foregoing observations, the eggs may be evaluated as follows:

1. If $T_{Measured}(i,j) \geq T_{Predicted}(i,j) - Y$ degrees, then the egg is classified as live; and 2. If $T_{Measured}(i,j) < T_{Predicted}(i,j) - Y$ degrees, then the egg is classified as non-live where Y is a constant select to account for the expected variance between $T_{Measured}(i,j)$ and $T_{Predicted}(i,j)$ due to the presence of non-live, non-clear eggs (i.e., the presence of non-live egg temperatures in the ATDS). Y is also selected to reflect the desired bias against discarding live eggs as weighed against the desired bias against retaining (and treating) dead or rotted eggs. Typically, Y will be about 1° F.

The eggs earlier identified as clear eggs using the light candling data are not classified using the TTM.

The foregoing method (Method B) using a TTM may be modified (hereinafter, the modified method is referred to as "Method C"). Rather than adding X degrees to the clear eggs in creating the ATDS, the temperatures of the clear eggs may be excluded from the ATDS in the same manner as the temperatures of the empty and upside-down eggs.

The foregoing Method B and Method C effectively eliminate the clear and other non-live egg temperatures from the classification determination, thereby providing the improvements in accuracy and other advantages discussed above with regard to Method A. Additionally, by using the TTM (i.e., the predicted temperatures), the methods compensate or correct the temperatures of the eggs for relative locations in the flat (i.e., different micro-environments).

Temperature trends may be determined and Temperature Trend Maps may be generated to correct or compensate the measured egg temperatures for different micro-environments without using the light candling data, as well. For example, each of the aforedescribed Methods A, B and C may be modified such that the identification of clear eggs (or other non-live eggs identifiable by light candling) is not required.

Method B may be modified (hereinafter, the modified method is referred to as "Method D") such that the TTM is generated using the measured temperatures of all eggs (or, more preferably, all of the eggs except those identified as upside-down). Restated, in Method D, Method B may be modified such that the assigned $T_{adj}(i,j)$ for all non-upside-down eggs will equal the $T_{Measured}(i,j)$.

Similarly, the measured egg temperatures may be corrected or compensated for differences in micro-environments as described with regard to Method A except that the temperature correction is performed using the measured temperatures of all of the eggs (or, more preferably, all of the eggs except those identified as upside-down) rather than only non-clears or only the probable lives and rots (R) (hereinafter, the modified method is referred to as "Method E"). The corrected egg temperature of each egg may then be evaluated to determine if the egg is live or non-live using one of the various methods described in U.S. Pat. No. 4,914,672 to Hebrank or other suitable methods. For example, the individual corrected egg temperatures, rather than the measured temperatures, may be compared to a threshold temperature to classify the eggs as live and non-live.

Each of the foregoing methods of correcting or compensating the egg temperatures may be accomplished by evaluating the entire flat of eggs or, alternatively, by evaluating separate segments or portions of a given flat independently. For example, a 7-egg by 24-egg flat may be evaluated as two 7 by 12 segments, with the selected method of evaluating and classifying the eggs being performed on each segment as if it were a separate flat.

Using the foregoing methods, each of the eggs 2 in the flat is classified as live or non-live. The non-live eggs may be further classified as {clear or early dead} versus {mid-dead or late dead (depending on the day of candling) or rot} versus {missing} versus {empty} using the light candling data.

After the eggs are identified as live, clear, empty, missing, early dead, mid-dead, late dead or rot, the results are displayed graphically on the display 42 (e.g., a screen of a PC computer monitor) along with cumulative statistics for a group or flock of eggs (Block 620). Such cumulative statistics may be assembled, calculated and/or estimated by the controller using the classification data. The cumulative statistics may include, for each group, flock or flat, fertility percentage, early dead percentage, mid-dead percentage, upside-down percentage and percentage of rots. These statistics may be useful to monitor and evaluate hatchery and incubator operation.

The flat is then placed on the conveyor 7B which transports the flat of classified eggs through the sorting station 60. Preferably, the eggs remain in a fixed array. The sorting station 60 physically removes the clear and early dead eggs from the flat 12 and directs them to a collector (Block 622). The clear and early dead eggs may be used for purposes other than hatching broilers. For example, the clear and early dead eggs may be used in the production of shampoo and dog food and are more desirable when not contaminated with rot eggs. The sorting station 60 may also remove the empty, rot, mid-dead and late dead eggs and direct them to a separate collector.

The sorting station 60 may employ suction-type lifting devices as disclosed in U.S. Pat. No. 4,681,063 or in U.S. Pat. No. 5,017,003 to Keromnes et al., the disclosures of which are hereby incorporated by reference herein in their entireties. Any other suitable means for removing the eggs may be used as well, such apparatus being known to those of ordinary skill in the art.

The sorting station preferably operates automatically and robotically. Alternatively, the selected eggs may be identified on the display 42, optionally marked, and removed by hand. The sorting station 60 may be provided downstream of the treatment station 50, in which case the non-live eggs will pass through the treatment station but will not be inoculated.

Following the sorting station 60, the flat 12 is placed on the conveyor 7C which transports the flat 12 through the treatment station 50 (Block 624). The flat will at this time hold all of the eggs which have not been removed, namely those eggs classified as live eggs. The eggs are preferably maintained in their original, fixed array positions in the flat. The treatment station 50 may treat the remaining eggs in any desired, suitable manner. It is particularly contemplated that the treatment station 50 may inject the remaining, "live" eggs with a treatment substance.

As used herein, the term "treatment substance" refers to a substance that is injected into an egg to achieve a desired result. Treatment substances include but are not limited to vaccines, antibiotics, vitamins, virus, and immunomodulatory substances. Vaccines designed for in ovo use to combat outbreaks of avian diseases in the hatched birds are commercially available. Typically the treatment substance is dispersed in a fluid medium, e.g., is a fluid or emulsion, or is a solid dissolved in a fluid, or a particulate dispersed or suspended in a fluid.

As used herein, the term "needle" or "injection needle" refers to an instrument designed to be inserted into an egg to deliver a treatment substance into the interior of the egg. A number of suitable needle designs will be apparent to those skilled in the art. The term "injection tool" as used herein refers to a device designed to both pierce the shell of an avian egg and inject a treatment substance therein. Injection tools may comprise a punch for making a hole in the egg shell, and an injection needle that is inserted through the hole made by the punch to inject a treatment substance in ovo. Various designs of injection tools, punches, and injection needles will be apparent to those in the art.

As used herein, "in ovo injection" refers to the placing of a substance within an egg prior to hatch. The substance may be placed within an extraembryonic compartment of the egg (e.g., yolk sac, amnion, allantois) or within the embryo itself. The site into which injection is achieved will vary depending on the substance injected and the outcome desired, as will be apparent to those skilled in the art.

Figure 7:
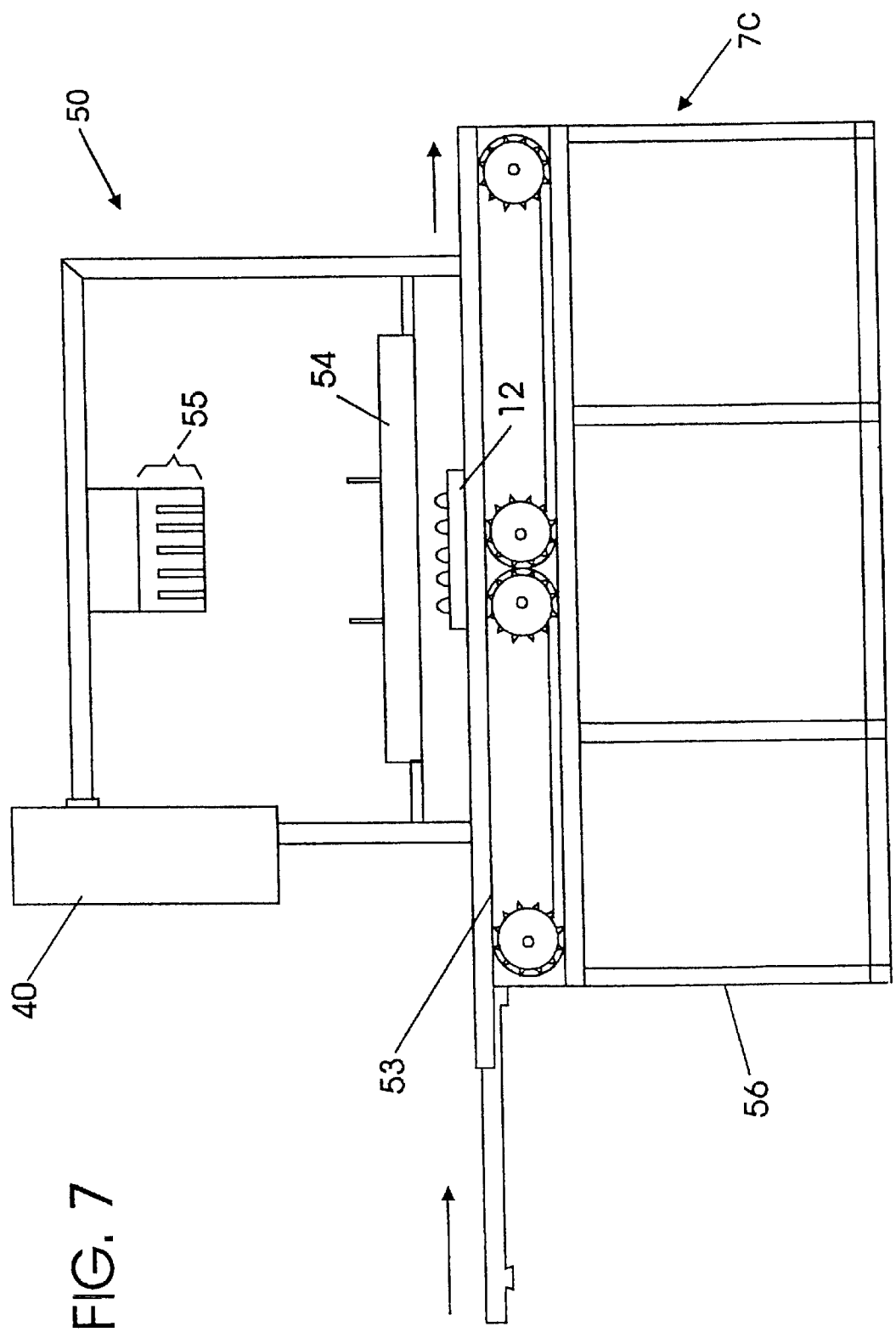
FIG. 7 is a side elevational view of a treatment station forming a part of the apparatus of FIG. 1.

FIG. 7 schematically illustrates a treatment station 50 that can be used to carry out the selective injection methods of the present invention. The treatment station 50 comprises at least one reservoir 57 for holding the treatment substance to be injected into the eggs identified as suitable. A conveyor belt 53 forming a part of the conveyor 7C is configured to move the flat 12 of eggs 2. The direction of travel of the eggs along the conveyors is indicated by arrows in FIG. 7.

As the flat 12 of eggs is conveyed through the treatment station 50, the controller 40 selectively generates an injection signal to the treatment station 50 to inject those eggs which have been classified by the controller 40 as live eggs or eggs otherwise suitable for injection. As used herein, the "selective generation of an injection signal" (or the generation of a selective injection signal), refers to the generation by the controller of a signal that causes injection only of those eggs identified by the classifier as suitable for injection. As will be apparent to those skilled in the art, generation of a selective injection signal may be achieved by various approaches, including generating a signal that causes the injection of suitable eggs, or generating a signal that prevents the injection of non-suitable eggs.

A preferred injector for use in the methods described herein is the INOVOJECT® automated injection device (Embrex, Inc., Research Triangle Park, N.C.). However, any in ovo injection device capable of being operably connected, as described herein, to the controller 40 is suitable for use in the present methods. Suitable injection devices preferably are designed to operate in conjunction with commercial egg carrier devices or flats, examples of which are described herein above.

Preferably, the injector comprises a plurality of injection needles, to increase the speed of operation. The injector may comprise a plurality of injection needles which operate simultaneously or sequentially to inject a plurality of eggs, or alternatively may comprise a single injection needle used to inject a plurality of eggs.

Figure 8:
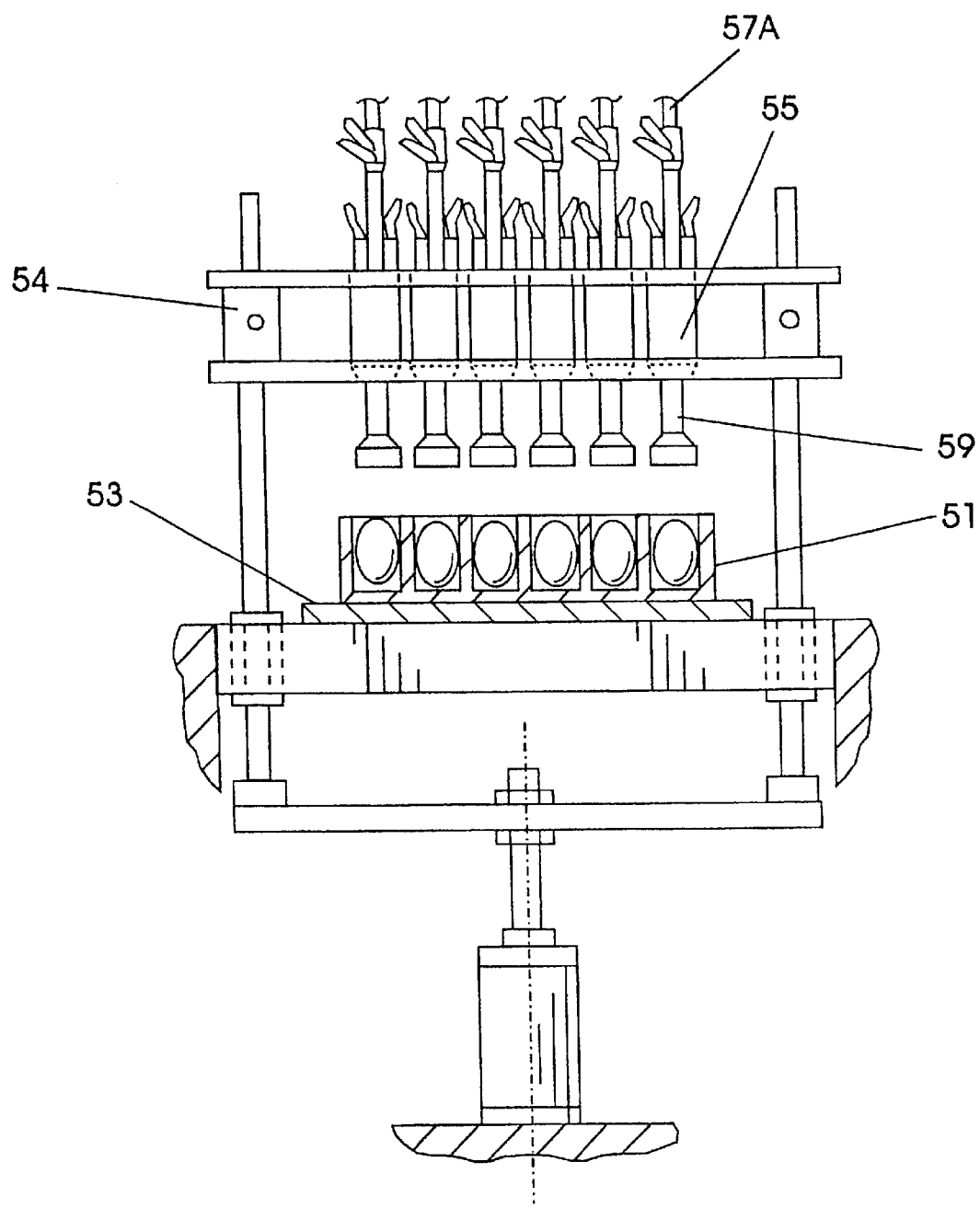
FIG. 8 is an enlarged view of an injection head of the treatment station of FIG. 7.

As shown in FIG. 8, the treatment station 50 may comprise an injection head 54 in which the injection needles (not shown) are situated. The injection head or the injection needles are capable of movement in order to inject eggs. Each injection needle is in fluid connection with the reservoir 57 containing the treatment substance to be injected. A single reservoir may supply all of the injection needles in the injection head, or multiple reservoirs may be utilized. An exemplary injection head is shown in FIG. 8, where the conveyor belt 53 has aligned the egg flat 12 with the injection head 54. Each injection needle (not shown) is housed in a guiding tube 59 designed to rest against the exterior of an egg. Each injection needle is operably connected to a fluid pump 55. Each fluid pump is in fluid connection with tubing 57A, which is in fluid connection with the reservoir 57 containing the treatment substance. Suitable injection devices are described in U.S. Pat. No. 4,681,063 to Hebrank, U.S. Pat. No. 4,903,635 to Hebrank, U.S. Pat. No. 5,136,979 to Paul and U.S. Pat. No. 5,176,101 to Paul.

Preferably, the eggs suitable for injection remain in the same compartments in the same flat throughout the classifying, sorting and treatment steps so that the eggs are prevented from changing their positions relative to other eggs while passing from the candling station 8 to the injector. Preferably, each needle of the injection head 54 is aligned with one compartment of the egg flat (i.e., is aligned with the egg contained therein).

The selective delivery of treatment substance only to eggs identified as suitable can be accomplished by any of various means that will be apparent to those skilled in the art. Examples include, but are not limited to, individually controlled fluid pumps, e.g., solenoid-operated pumps; or individual valves that control the flow of treatment substance from a reservoir to an associated fluid pump. Alternatively, selective delivery of treatment substance may be accomplished by individual control of injection needles or egg shell punches, so that punches and/or needles do not enter those eggs identified as non-suitable. As a further alternative, the eggs may be rearranged in the flat (for example, all live eggs re-positioned to one end of the flat) to correspond to the locations of the needles or to otherwise simplify the vaccine dispensing system.

The treatment station 50 may be designed so that eggs can pass by in an uninterrupted flow. Where the eggs must come to a halt to be injected, it will be apparent to those skilled in the art that the use of an apparatus comprising more than one injection head may be desirable to increase the speed of the overall operation.

The conveying system 7 may allow independent movement of conveyors 7A, 7B, 7C so that an item placed on the conveyor 7A will pass to subsequent conveyors 7B and 7C automatically. The conveyor 7A may pass egg flats under the candling system 8 in a continuous flow, whereas the downstream conveyor 7C may be used to move an egg flat to a position aligned with the injection head 54 and halt while the eggs are injected. Movement of the conveyors 7A, 7B, and 7C may be under guidance of programmed or computerized control means or manually controlled by an operator. In a preferred embodiment, the conveyor belt 53 is supported by a frame 56 which raises the conveying means to a height at which egg flats can be conveniently loaded.

Those skilled in the art will appreciate that many conveyor designs will be suitable for use in the present invention. The conveyors 7A, 7B, 7C may be in the form of guide rails designed to receive and hold an egg flat, or a conveyor belt upon which an egg flat can be placed. Conveyor belts or guide rails may include stops or guides that act to evenly space a plurality of egg flats along the conveying path.

The present invention is described in greater detail in the following non-limiting Examples.

EXAMPLE 1

Figure 9:
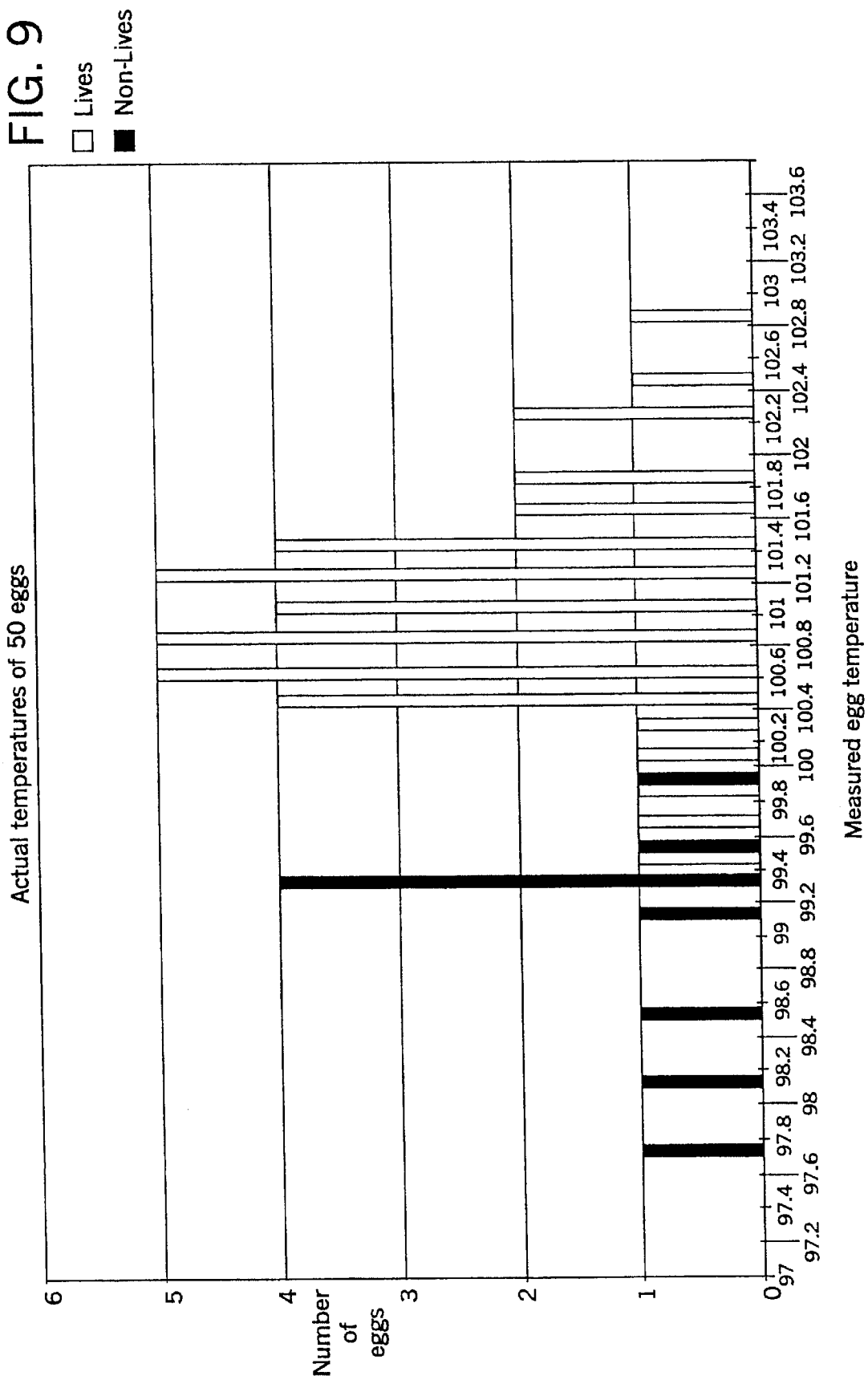
FIG. 9 is a histogram of a distribution of measured temperatures of an exemplary array of eggs.

Each egg of a ten row by five column (10×5) array of turkey eggs was thermal candled and light candled. Each egg was thereafter broken open and inspected or otherwise evaluated to positively identify those eggs which as actually live (L) or non-live (NL). Table 1 below lists the measured temperatures of the eggs, along with their respective positions (i,j). FIG. 9 is a histogram graphically showing the distribution of the measured, uncorrected egg temperatures.

The measured temperatures were used to identify the upside-down and empty eggs by calculating the average temperature of all of the eggs and classifying those eggs having temperatures at least 5 degrees less than the average temperature as empty or upside-down. The egg temperatures were corrected or compensated for location in the array using the correction method described above with regard to Method E, i.e., all of the eggs were used in the calculation except those eggs classified as empty or upside-down eggs. That is, the temperatures of clear, early dead and mid-dead eggs, to the extent present, were used in the correction calculations. The temperatures corrected in this manner, without the benefit of light candling, are listed in Table 1 and graphically displayed in FIG. 10.

Figure 11:
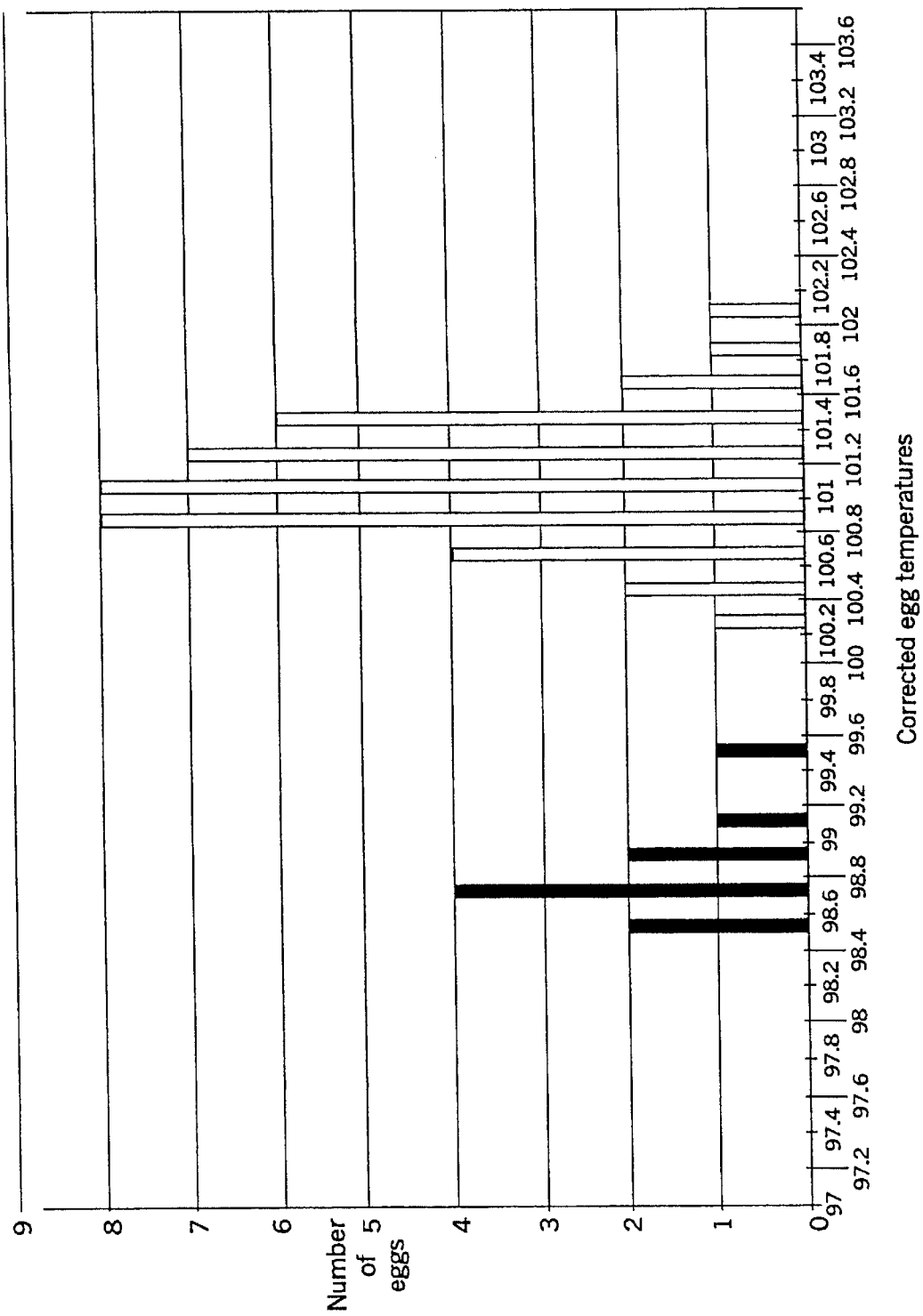
FIG. 11 is a histogram of the distribution of corrected temperatures of the array of eggs of FIG. 9, wherein the temperatures have been corrected using light candling data.

The measured egg temperatures were also corrected or compensated by the Method A described above, i.e., using the light candling data. The eggs were classified using the light candling data as either clear, early dead or mid-dead (collectively, "C") or, alternatively, dark ("D"). The measured temperatures were then corrected using only those eggs not classified as empty, upside-down, clear, early dead or mid-dead in the manner described above. Table 1 lists the temperatures corrected using the light candling data. FIG. 11 graphically shows the distribution of these temperatures.

TABLE 1

| EGG No. | Row | Column | Actual Condition (L = live; NL = non-live) | Measured temp. | Light measurement (C = Clear; D = Dark) | Temp. corrected without light data (° F.) | Temp. corrected with light data (° F.) |
|---|---|---|---|---|---|---|---|
| 1 | 1 | 1 | L | 101.15 | D | 100.56 | 101.16 |
| 2 | 1 | 2 | L | 101.64 | D | 100.62 | 100.86 |
| 3 | 1 | 3 | L | 102.04 | D | 100.79 | 100.95 |
| 4 | 1 | 4 | L | 102.32 | D | 101.06 | 101.4 |
| 5 | 1 | 5 | L | 100.44 | D | 99.37 | 100.17 |
| 6 | 2 | 1 | L | 101.22 | D | 101 | 101.33 |
| 7 | 2 | 2 | L | 101.46 | D | 100.81 | 100.78 |
| 8 | 2 | 3 | NL | 99.36 | C | 98.49 | 98.37 |
| 9 | 2 | 4 | L | 102.64 | D | 101.75 | 101.82 |
| 10 | 2 | 5 | L | 100.94 | D | 100.24 | 100.76 |
| 11 | 3 | 1 | L | 100.77 | D | 100.87 | 100.99 |
| 12 | 3 | 2 | L | 101.25 | D | 100.92 | 100.68 |
| 13 | 3 | 3 | L | 101.24 | D | 100.69 | 100.36 |
| 14 | 3 | 4 | L | 101.46 | D | 100.89 | 100.75 |
| 15 | 3 | 5 | L | 100.98 | D | 100.6 | 100.91 |
| 16 | 4 | 1 | L | 100.93 | D | 101.3 | 101.27 |
| 17 | 4 | 2 | NL | 99.11 | C | 99.05 | 98.67 |
| 18 | 4 | 3 | NL | 99.08 | C | 98.8 | 98.33 |
| 19 | 4 | 4 | L | 102.11 | D | 101.81 | 101.52 |
| 20 | 4 | 5 | L | 100.51 | D | 100.4 | 100.57 |
| 21 | 5 | 1 | L | 100.55 | D | 101.13 | 101.03 |
| 22 | 5 | 2 | NL | 99.16 | C | 99.31 | 98.86 |
| 23 | 5 | 3 | NL | 99.03 | C | 98.96 | 98.42 |
| 24 | 5 | 4 | NL | 99.66 | C | 99.57 | 99.21 |
| 25 | 5 | 5 | L | 100.69 | D | 100.79 | 100.89 |
| 26 | 6 | 1 | L | 99.57 | D | 100.31 | 100.21 |
| 27 | 6 | 2 | L | 101.08 | D | 101.39 | 100.93 |
| 28 | 6 | 3 | NL | 98.92 | C | 99.01 | 98.46 |
| 29 | 6 | 4 | L | 101.3 | D | 101.37 | 101.01 |
| 30 | 6 | 5 | L | 100.58 | D | 100.84 | 100.93 |
| 31 | 7 | 1 | L | 100.33 | D | 101.17 | 101.14 |
| 32 | 7 | 2 | L | 100.62 | D | 101.03 | 100.64 |
| 33 | 7 | 3 | L | 100.95 | D | 101.14 | 100.66 |
| 34 | 7 | 4 | L | 101.77 | D | 101.94 | 101.65 |

TABLE 1-continued

| EGG No. | Row | Column | Actual Condition (L = live; NL = non-live) | Measured temp. | Light measurement (C = Clear; D = Dark) | Temp. corrected without light data (° F.) | Temp. corrected with light data (° F.) |
|---|---|---|---|---|---|---|---|
| 35 | 7 | 5 | L | 100.56 | D | 100.92 | 101.08 |
| 36 | 8 | 1 | NL | 97.52 | C | 98.41 | 98.51 |
| 37 | 8 | 2 | L | 100.26 | D | 100.72 | 100.46 |
| 38 | 8 | 3 | L | 101.11 | D | 101.35 | 101 |
| 39 | 8 | 4 | L | 101.07 | D | 101.29 | 101.13 |
| 40 | 8 | 5 | NL | 97.84 | C | 98.25 | 98.55 |
| 41 | 9 | 1 | L | 100.15 | D | 101.04 | 101.34 |
| 42 | 9 | 2 | NL | 98.38 | C | 98.84 | 98.78 |
| 43 | 9 | 3 | L | 100.71 | D | 100.95 | 100.8 |
| 44 | 9 | 4 | L | 101.16 | D | 101.38 | 101.42 |
| 45 | 9 | 5 | L | 100.38 | D | 100.79 | 101.29 |
| 46 | 10 | 1 | L | 99.73 | D | 100.56 | 101.13 |
| 47 | 10 | 2 | L | 99.98 | D | 100.38 | 100.6 |
| 48 | 10 | 3 | L | 100.36 | D | 100.54 | 100.67 |
| 49 | 10 | 4 | L | 100.75 | D | 100.91 | 101.22 |
| 50 | 10 | 5 | L | 99.35 | D | 99.7 | 100.47 |

Figure 10:
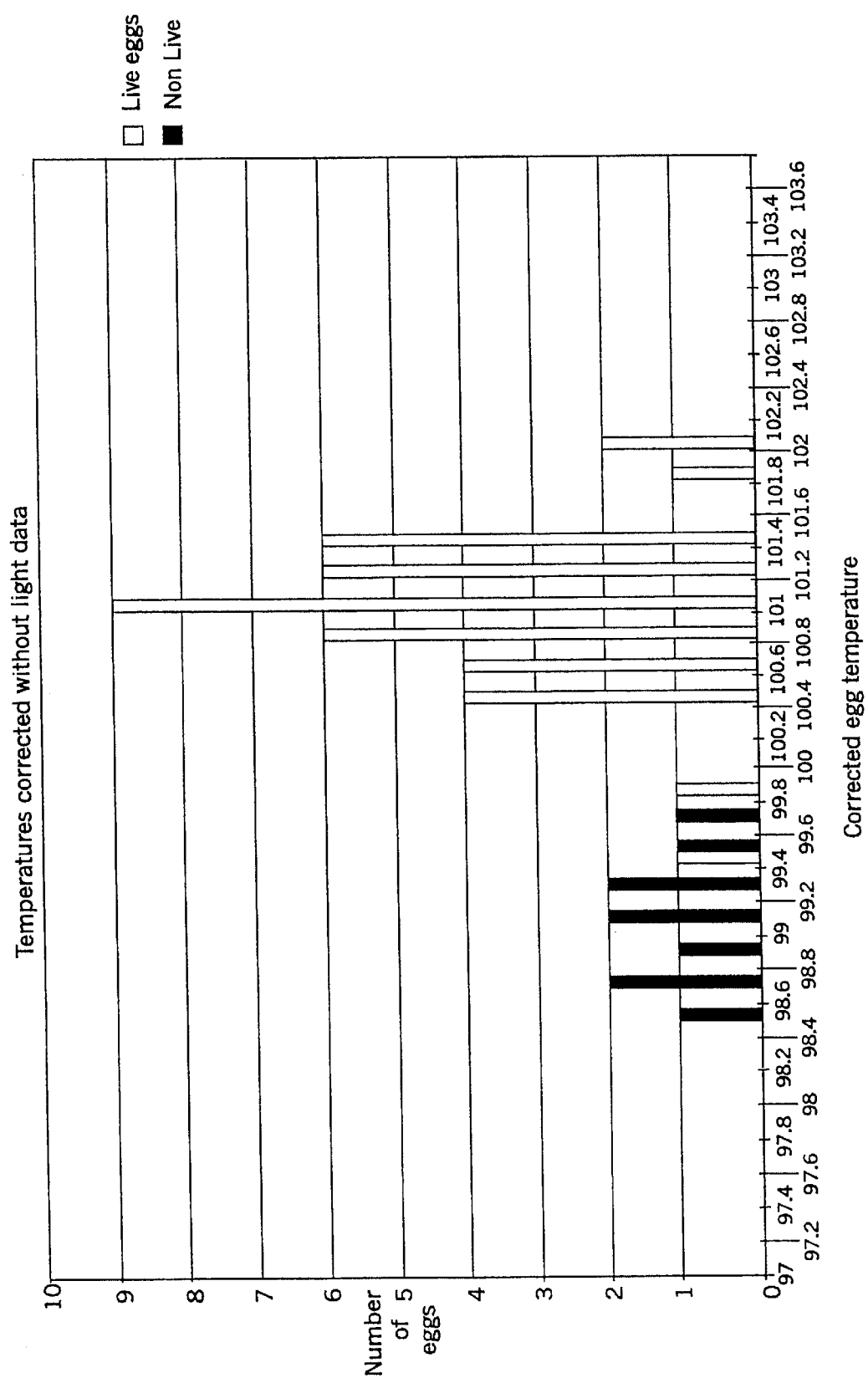
FIG. 10 is a histogram of the distribution of corrected temperatures of the array of eggs of FIG. 9, wherein the temperatures have been corrected without using light candling data.

Comparing FIGS. 9 and 10, it will be appreciated that correction or compensation of the measured temperatures reduces the overlap between the temperatures of the actual live and non-live eggs which are used to distinguish the live eggs from the non-live eggs. Comparing FIGS. 10 and 11, it will be appreciated that correction of the measured temperatures using light data reduces the overlap between the temperatures of the actual live and non-live eggs which are used to distinguish the live eggs from the non-live eggs as compared to correction without light candling.

Thus, the accuracy of the temperature correction and the advantages of removing clear and early-dead eggs from the calculation procedure is demonstrated by temperature histograms of FIGS. 9, 10 and 11 that compare the results of no correction, correction based upon all eggs except empty and upside-down eggs, and correction without using clears and early-deads in the calculation of the predicted and mean temperatures. As will be readily apparent, the correction procedure makes live/dead classification more distinct and, more particularly, removing the clear eggs from the calculation significantly improves classification accuracy.

EXAMPLE 2

Using the information as set forth in Table 2 below, the eggs were evaluated using Method D described above to generate a TTM including a predicted temperature ($T_{Predicted}(i,j)$) for each egg using the temperatures of all of the eggs except those identified as upside-down eggs. These predicted temperatures are listed in Table 2. The predicted temperatures were then compared to the corresponding measured temperatures to classify the eggs as live and non-live. The constant Y was selected as 1.0° F. The resulting corresponding egg classifications are also listed in Table 2. Comparing the actual conditions of the 50 eggs to the determined classifications, it will be seen that only one live egg was classified as non-live, and only one non-live egg was classified as a live egg.

Using the information as set forth in Table 2, the eggs were also evaluated using Method B as described above to generate a TTM including a predicted temperature for each egg using all of the eggs except those identified as upside-down. Additionally, the temperatures of the eggs identified as clear were adjusted using a constant value of 2.0° F. for X. The predicted temperatures calculated for each egg are listed in Table 2. The predicted temperatures were then compared to the corresponding measured temperatures to classify the eggs as live and non-live. The constant Y was selected as 1.0° F. The resulting corresponding egg classifications are also listed in Table 2. Comparing the actual conditions of the 50 eggs to the determined classifications, it will be seen that no live eggs were classified as non-live, and no non-live eggs were classified as live eggs.

TABLE 2

| EGG No. | Row | Column | Actual Condition (L = live; NL = non-live) | Measured temp. | Light measurement (C = Clear; D = Dark) | Predicted temp. without light data | Egg prediction for Y = 1° F. (without light) | Predicted temp. with light data | Egg prediction for Y = 1° F. (with light) |
|---|---|---|---|---|---|---|---|---|---|
| 1 | 1 | 1 | L | 101.15 | D | 101.07 | L | 100.89 | L |
| 2 | 1 | 2 | L | 101.64 | D | 101.50 | L | 101.68 | L |
| 3 | 1 | 3 | L | 102.04 | D | 101.73 | L | 101.99 | L |
| 4 | 1 | 4 | L | 102.32 | D | 101.74 | L | 101.82 | L |
| 5 | 1 | 5 | L | 100.44 | D | 101.55 | NL | 101.17 | L |
| 6 | 2 | 1 | L | 101.22 | D | 100.70 | L | 100.79 | L |
| 7 | 2 | 2 | L | 101.46 | D | 101.13 | L | 101.58 | L |
| 8 | 2 | 3 | NL | 99.36 | C | 101.35 | NL | 101.89 | NL |
| 9 | 2 | 4 | L | 102.64 | D | 101.37 | L | 101.72 | L |
| 10 | 2 | 5 | L | 100.94 | D | 101.18 | L | 101.08 | L |
| 11 | 3 | 1 | L | 100.77 | D | 100.38 | L | 100.68 | L |
| 12 | 3 | 2 | L | 101.25 | D | 100.81 | L | 101.47 | L |
| 13 | 3 | 3 | L | 101.24 | D | 101.03 | L | 101.78 | L |
| 14 | 3 | 4 | L | 101.46 | D | 101.05 | L | 101.61 | L |
| 15 | 3 | 5 | L | 100.98 | D | 100.86 | L | 100.97 | L |
| 16 | 4 | 1 | L | 100.93 | D | 100.11 | L | 100.56 | L |
| 17 | 4 | 2 | NL | 99.11 | C | 100.54 | NL | 101.34 | NL |
| 18 | 4 | 3 | NL | 99.08 | C | 100.76 | NL | 101.65 | NL |
| 19 | 4 | 4 | L | 102.11 | D | 100.78 | L | 101.49 | L |
| 20 | 4 | 5 | L | 100.51 | D | 100.59 | L | 100.84 | L |
| 21 | 5 | 1 | L | 100.55 | D | 99.90 | L | 100.42 | L |
| 22 | 5 | 2 | NL | 99.16 | C | 100.33 | NL | 101.20 | NL |
| 23 | 5 | 3 | NL | 99.03 | C | 100.55 | NL | 101.51 | NL |
| 24 | 5 | 4 | NL | 99.66 | C | 100.57 | L | 101.35 | NL |
| 25 | 5 | 5 | L | 100.69 | D | 100.38 | L | 100.70 | L |

TABLE 2-continued

| EGG No. | Row | Column | Actual Condition (L = live; NL = non-live) | Measured temp. | Light measurement (C = Clear; D = Dark) | Predicted temp. without light data | Egg prediction for Y = 1° F. (without light) | Predicted temp. with light data | Egg prediction for Y = 1° F. (with light) |
|---|---|---|---|---|---|---|---|---|---|
| 26 | 6 | 1 | L | 99.57 | D | 99.74 | L | 100.26 | L |
| 27 | 6 | 2 | L | 101.08 | D | 100.17 | L | 101.05 | L |
| 28 | 6 | 3 | NL | 98.92 | C | 100.39 | NL | 101.36 | NL |
| 29 | 6 | 4 | L | 101.30 | D | 100.41 | L | 101.19 | L |
| 30 | 6 | 5 | L | 100.58 | D | 100.22 | L | 100.55 | L |
| 31 | 7 | 1 | L | 100.33 | D | 99.64 | L | 100.09 | L |
| 32 | 7 | 2 | L | 100.62 | D | 100.07 | L | 100.88 | L |
| 33 | 7 | 3 | L | 100.95 | D | 100.29 | L | 101.19 | L |
| 34 | 7 | 4 | L | 101.77 | D | 100.31 | L | 101.02 | L |
| 35 | 7 | 5 | L | 100.56 | D | 100.12 | L | 100.38 | L |
| 36 | 8 | 1 | NL | 97.52 | C | 99.59 | NL | 99.91 | NL |
| 37 | 8 | 2 | L | 100.26 | D | 100.02 | L | 100.70 | L |
| 38 | 8 | 3 | L | 101.11 | D | 100.24 | L | 101.01 | L |
| 39 | 8 | 4 | L | 101.07 | D | 100.26 | L | 100.84 | L |
| 40 | 8 | 5 | NL | 97.84 | C | 100.07 | NL | 100.19 | NL |
| 41 | 9 | 1 | L | 100.15 | D | 99.59 | L | 99.71 | L |
| 42 | 9 | 2 | NL | 98.38 | C | 100.02 | NL | 100.50 | NL |
| 43 | 9 | 3 | L | 100.71 | D | 100.24 | L | 100.81 | L |
| 44 | 9 | 4 | L | 101.16 | D | 100.26 | L | 100.64 | L |
| 45 | 9 | 5 | L | 100.38 | D | 100.07 | L | 99.99 | L |
| 46 | 10 | 1 | L | 99.73 | D | 99.65 | L | 99.50 | L |
| 47 | 10 | 2 | L | 99.98 | D | 100.08 | L | 100.28 | L |
| 48 | 10 | 3 | L | 100.36 | D | 100.30 | L | 100.59 | L |
| 49 | 10 | 4 | L | 100.75 | D | 100.32 | L | 100.43 | L |
| 50 | 10 | 5 | L | 99.35 | D | 100.13 | L | 99.78 | L |

The use of both the light candling sensors and the thermal candling sensors also facilitates the identification of faulty or dirty thermal or light sensors.

While certain preferred light and thermal candling systems have been described herein, it will be appreciated that any suitable means for assessing the opacities and temperatures of the eggs may be used. It is intended that all such means shall be included in the present invention, means and methods using candling being merely preferred means and methods for assessing the opacities and temperatures of the eggs in accordance with the invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for classifying poultry eggs, said method comprising the steps of:
    measuring the opacities of the eggs;
    measuring the temperatures of the eggs; and
    classifying the eggs as a function of both the opacities of the eggs and the temperatures of the eggs.

2. The method of claim 1 wherein said step of classifying includes distinguishing between clear eggs and at least one other class of eggs.

3. The method of claim 1 including the step of injecting eggs of a prescribed class with a treatment substance.

4. The method of claim 1 including the step of reporting information relating to the egg classifications.

5. The method of claim 1 including the step of separating different classes of the eggs from one another.

6. The method of claim 1 wherein said step of classifying includes:
    classifying the eggs into first and second mutually exclusive groups using the opacities of the eggs;
    correcting the temperatures of the second group of eggs for relative egg locations using the temperatures of the second group of eggs and not the temperatures of the first group of eggs; and
    identifying live eggs of the plurality of eggs using the corrected temperatures of the second group of eggs.

7. The method of claim 1 wherein said step of classifying includes:
    classifying the eggs into first and second mutually exclusive groups using the opacities of the eggs; and
    classifying the second group of eggs using the temperatures of the second group of eggs and the identification of the first group of eggs.

8. The method of claim 7 further including correcting the temperatures of the second group of eggs for relative egg locations using only the temperatures of eggs of the second group.

9. The method of claim 1 wherein said step of classifying includes:
    classifying the eggs into first and second mutually exclusive groups of the opacities of the eggs; and
    classifying the second group of eggs using the temperatures of the second group of eggs and not the temperatures of the first group of eggs.

10. The method of claim 9 further including correcting the temperatures of the second group of eggs for relative egg locations using the temperatures of the second group of eggs and not the temperatures of the first group of eggs.

11. An apparatus for classifying a plurality of poultry eggs each having an opacity and a temperature, said apparatus comprising:

means for detecting the opacities of the eggs;

means for detecting the temperatures of the eggs; and means for classifying the eggs using both the opacities of the eggs and the temperatures of the eggs.

12. The apparatus of claim 11 wherein said means for classifying further distinguished between clear eggs and at least one other class of eggs.

13. The apparatus of claim 11 wherein said treating means includes an injector operative to inject the prescribed class of the eggs with a treatment substance.

14. The apparatus of claim 11 including means for reporting information relating to the egg classifications.

15. The apparatus of claim 11 including sorting means operative to separate different classes of the eggs from one another.

16. The apparatus of claim 11 wherein said means for classifying:

classifies the eggs into first and second mutually exclusive groups using the opacities of the eggs;

corrects the temperatures of the first group of eggs for relative egg locations using the temperatures of the first group of eggs and not the temperatures of the second grouped of eggs; and identifies live eggs of the plurality of eggs using the corrected temperatures of the first group of eggs.

17. The apparatus of claim 11 wherein said means for classifying:

classifies the eggs into first and second mutually exclusive using the opacities of the eggs; and further classifies the second group of eggs using the temperatures of the eggs and the identification of the first group of eggs.

18. The apparatus of claim 17 wherein said means for classifying corrects the temperatures of the eggs for relative egg locations using only the temperatures of eggs of the second group.

19. The apparatus of claim 11 wherein said means for classifying:

classifies the eggs into first and second mutually exclusive groups using the opacities of the eggs; and further classifies the second group of eggs using the temperatures of the second group of eggs and not the temperatures of the first group of eggs.

20. The apparatus of claim 19 wherein said means for classifying corrects the temperatures of the second group of the eggs for relative egg locations using the temperatures of the second group of eggs and not the temperatures of the first group of eggs.

* * * * *

UNITED STATES PATENT AND TRADEMARK OFFICE
CERTIFICATE OF CORRECTION

PATENT NO. : 6,427,844 B2
DATED : August 6, 2002
INVENTOR(S) : John H. Hebrank

It is certified that error appears in the above-identified patent and that said Letters Patent is hereby corrected as shown below:

Column 26,
Line 64, should read -- sive groups using the opacities of the eggs; and --

Column 28,
Line 2, should read -- group of eggs; and --
Line 8, should read -- groups using the opacities of the eggs; and... --

Signed and Sealed this

Eleventh Day of February, 2003

JAMES E. ROGAN
*Director of the United States Patent and Trademark Office*